United States Patent
Kvamme et al.

(10) Patent No.: US 6,636,301 B1
(45) Date of Patent: *Oct. 21, 2003

(54) MULTIPLE BEAM INSPECTION APPARATUS AND METHOD

(75) Inventors: Damon F. Kvamme, San Jose, CA (US); Robert W. Walsh, Cupertino, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/636,129

(22) Filed: Aug. 10, 2000

(51) Int. Cl.[7] ............................................... G01N 21/00
(52) U.S. Cl. .................................. 356/237.2; 356/237.5
(58) Field of Search .......................... 356/237.1, 237.2, 356/237.3, 237.4, 237.5, 237.6, 600, 445, 446; 250/548, 559.3

(56) References Cited

U.S. PATENT DOCUMENTS

| | | | |
|---|---|---|---|
| 4,013,367 A | * | 3/1977 | Nagao et al. |
| 4,291,990 A | | 9/1981 | Takasu |
| 5,076,692 A | | 12/1991 | Neukermans et al. |
| 5,130,965 A | * | 7/1992 | Karaki et al. ............. 369/44.38 |
| 5,151,888 A | * | 9/1992 | Shikichi et al. .......... 369/44.32 |
| 5,268,747 A | | 12/1993 | Schoeps |
| 5,506,676 A | | 4/1996 | Hendler et al. |
| 5,563,702 A | | 10/1996 | Emery et al. |
| 5,569,929 A | | 10/1996 | Mizutani et al. |
| 5,576,825 A | | 11/1996 | Nakajima et al. |
| 5,602,400 A | * | 2/1997 | Kawashima ................. 250/548 |
| 5,737,072 A | | 4/1998 | Emery et al. |
| 5,995,220 A | * | 11/1999 | Suzuki ..................... 356/237.5 |
| 6,043,932 A | | 3/2000 | Kusunose |
| 6,084,716 A | | 7/2000 | Sanada et al. |
| 6,195,202 B1 | * | 2/2001 | Kusunose ................... 359/368 |
| 6,208,411 B1 | * | 3/2001 | Vaez-Iravani .......... 356/237.25 |

FOREIGN PATENT DOCUMENTS

| | | |
|---|---|---|
| EP | 0831295 | 3/1998 |
| WO | 99/38002 | 7/1999 |

* cited by examiner

*Primary Examiner*—Hoa Q. Pham
(74) *Attorney, Agent, or Firm*—Beyer Weaver & Thomas, LLP

(57) ABSTRACT

Disclosed is an optical inspection system for inspecting the surface of a substrate. The inspection system includes a light source for emitting a light beam along an optical axis and a first set of optical elements arranged for separating the light beam into a plurality of light beams, directing the plurality of light beams to intersection with the surface of the substrate, and focusing the plurality of light beams to a plurality of scanning spots on the surface of the substrate. The inspection system also includes a second set of optical elements adapted for collecting a plurality of transmitted light beams caused by the intersection of the plurality of light beams with the surface of the substrate and a light detector arrangement including individual light detectors that each receive individual ones of the plurality of transmitted light beams. The light detectors are arranged for sensing the light intensity of the transmitted light beams.

26 Claims, 11 Drawing Sheets

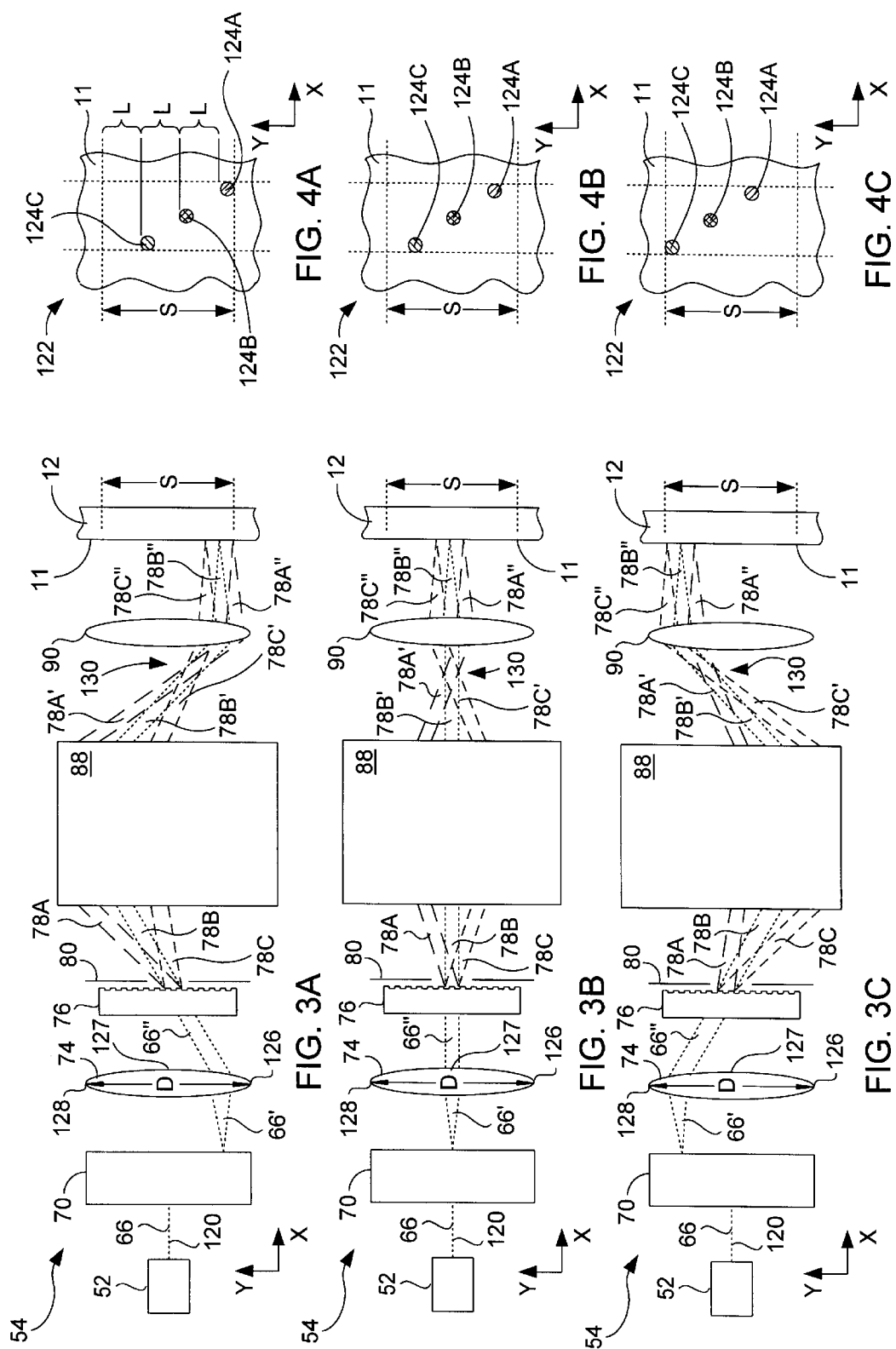

MULTIPLE BEAM INSPECTION APPARATUS AND METHOD

BACKGROUND OF THE INVENTION

The present invention relates to apparatus and methods for inspecting the surface of a substrate such as reticles, photomasks, wafers and the like (hereafter referred to generally as photomasks). More particularly, the present invention relates to an optical inspection system that can scan such a substrate at a high speed and with a high degree of sensitivity.

Integrated circuits are made by photolithographic processes, which use photomasks or reticles and an associated light source to project a circuit image onto a silicon wafer. The presence of defects on the surfaces of the photomasks is highly undesirable and adversely affects the resulting circuits. The defects can be due to, but not limited to, a portion of the pattern being absent from an area where it is intended to be present, a portion of the pattern being present in an area where it is not intended to be, chemical stains or residues from the photomask manufacturing processes which cause an unintended localized modification of the light transmission property of the photomask, particulate contaminates such as dust, resist flakes, skin flakes, erosion of the photolithographic pattern due to electrostatic discharge, artifacts in the photomask substrate such as pits, scratches, and striations, and localized light transmission errors in the substrate or pattern layer. Since it is inevitable that defects will occur, these defects have to be found and repaired prior to use. Blank substrates can also be inspected for defects prior to patterning. $Methods and apparatus for detecting defects have been around for some time. For example, inspection systems and methods utilizing laser light have been introduced and employed to various degrees to scan the surface of substrates such as photomasks, reticles and wafers. These laser inspection systems and methods generally include a laser source for emitting a laser beam, optics for focusing the laser beam to a scanning spot on the surface of the substrate, a stage for providing translational travel, collection optics for collecting either transmitted and/or reflected light, detectors for detecting either the transmitted and/or reflected light, sampling the signals at precise intervals and using this information to construct a virtual image of the substrate being inspected. By way of example, representative laser inspection systems are described in U.S. Pat. No. 5,563,702 to Emery et al., U.S. Pat. No. 5,737,072 to Emery et al., U.S. Pat. No. 5,572,598 to Wihl et al., and U.S. Pat. No. 6,052,478 to Wihl et al., each of which are incorporated herein by reference.

Although such systems work well, there are continuing efforts to improve their design to provide greater sensitivity and faster scanning speeds. That is, as the complexity of integrated circuits has increased, so has the demand on the inspection process. Both the need for resolving smaller defects and for inspecting larger areas have resulted in much greater magnification requirements and in much greater speed requirements, for example, in terms of number of pixels (picture elements) per second processed.

In view of the foregoing, there is a need for improved inspection techniques that provide increased scanning speeds.

SUMMARY OF THE INVENTION

Accordingly, the present invention addresses some of the above problems by providing improved apparatus and methods for performing an inspection. In general terms, the inspection system includes components arranged to generate a plurality of beams incident on a sample, such as a photomask. The inspection system also includes components for collecting and detecting a plurality of beams that are reflected or transmitted from the sample as a result of the incident beams.

In one embodiment, an optical inspection system for inspecting the surface of a substrate is disclosed. The inspection system includes a light source for emitting a light beam along an optical axis and a first set of optical elements arranged for separating the light beam into a plurality of light beams, directing the plurality of light beams to intersection with the surface of the substrate, and focusing the plurality of light beams to a plurality of scanning spots on the surface of the substrate. The inspection system also includes a second set of optical elements adapted for collecting a plurality of transmitted light beams caused by the intersection of the plurality of light beams with the surface of the substrate and a light detector arrangement including individual light detectors that each receive individual ones of the plurality of transmitted light beams. The light detectors are arranged for sensing the light intensity of the transmitted light beams.

In a specific implementation, the second set of optical elements includes transmitted light optics for collecting the transmitted light beams that pass through the substrate under inspection. In a more specific implementation, the transmitted light optics include at least a lens arrangement and a prism. The lens arrangement is arranged for focusing the plurality of transmitted light beams onto the prism, and the prism is arranged for directing individual ones of the transmitted light beams towards individual detectors of the light detector arrangement.

In one embodiment, the lens arrangement includes a first transmitted lens and a spherical aberration correction lens. The first transmitted lens are arranged for collecting and focusing the plurality of transmitted light beams, and the spherical aberration correction lens are arranged for maintaining image quality of the plurality of transmitted light beams. In one implementation, the prism includes a plurality of facets that correspond to each of the plurality of transmitted light beams. Each facet is arranged for directing an individual one of the plurality of light beams towards a corresponding individual light detector of the light detector arrangement.

In an alternative embodiment, another optical inspection system for inspecting a surface of a substrate is disclosed. The inspection system includes a transmitted light optical arrangement disposed along an optical axis. The transmitted optical arrangement includes at least a first lens and second lens, both of which are arranged to move along the optical axis, and a prism, which is arranged to move orthogonal to the optical axis. The transmitted light optical arrangement is arranged for directing a plurality of transmitted light beams, which are formed by scanning the substrate with a plurality of light beams, onto a plurality of light detectors. The inspection system further includes a control system for controlling the transmitted light optical arrangement so as to maintain separation of the plurality of beams on the light detectors. The control system includes at least a first lens drive, a second lens drive, and a prism drive. These control components are coupled to a control interface, which is arranged to control the drives. The first lens drive is arranged to actuate the movement of the first lens, and the second lens drive is arranged to actuate the movement of the second lens. The prism drive is arranged to actuate the movement of the prism.

DESCRIPTION OF THE DRAWINGS

The present invention is illustrated by way of example, and not by way of limitation, in the figures of the accompanying drawings and in which like reference numerals refer to similar elements and in which:

FIGS. 3A–C are side view illustrations of the light source and the inspection optics of FIG. 3, as light beams are scanned across the surface of the substrate, in accordance with one embodiment of the present invention.

FIGS. 4A–C are top view illustrations of the scanning spots produced by the inspection optics of FIGS. 3A–C, as light beams are scanned across the surface of the substrate, in accordance with one embodiment of the present invention.

DETAILED DESCRIPTION OF THE INVENTION

The present invention will now be described in detail with reference to a few specific embodiments thereof and as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order not to unnecessarily obscure the present invention.

The invention pertains to an optical inspection system for inspecting the surface of a substrate (or sample), and more particularly to an optical inspection system that can scan a substrate at a high speed and with a high degree of sensitivity. One aspect of the invention relates to increasing the number of scanning spots used to inspect the substrate. Another aspect of the invention relates to spatially separating each of the scanning spots used to inspect the substrate. Yet another aspect of the invention relates to collecting reflected and/or transmitted light caused by the intersection of scanning spots with the surface of the substrate. The invention is particularly useful for inspecting substrates, such as reticles and photomasks. Furthermore, the invention may be used to detect defects as well as to measure semiconductor device characteristics, such as line widths.

Figure 1:
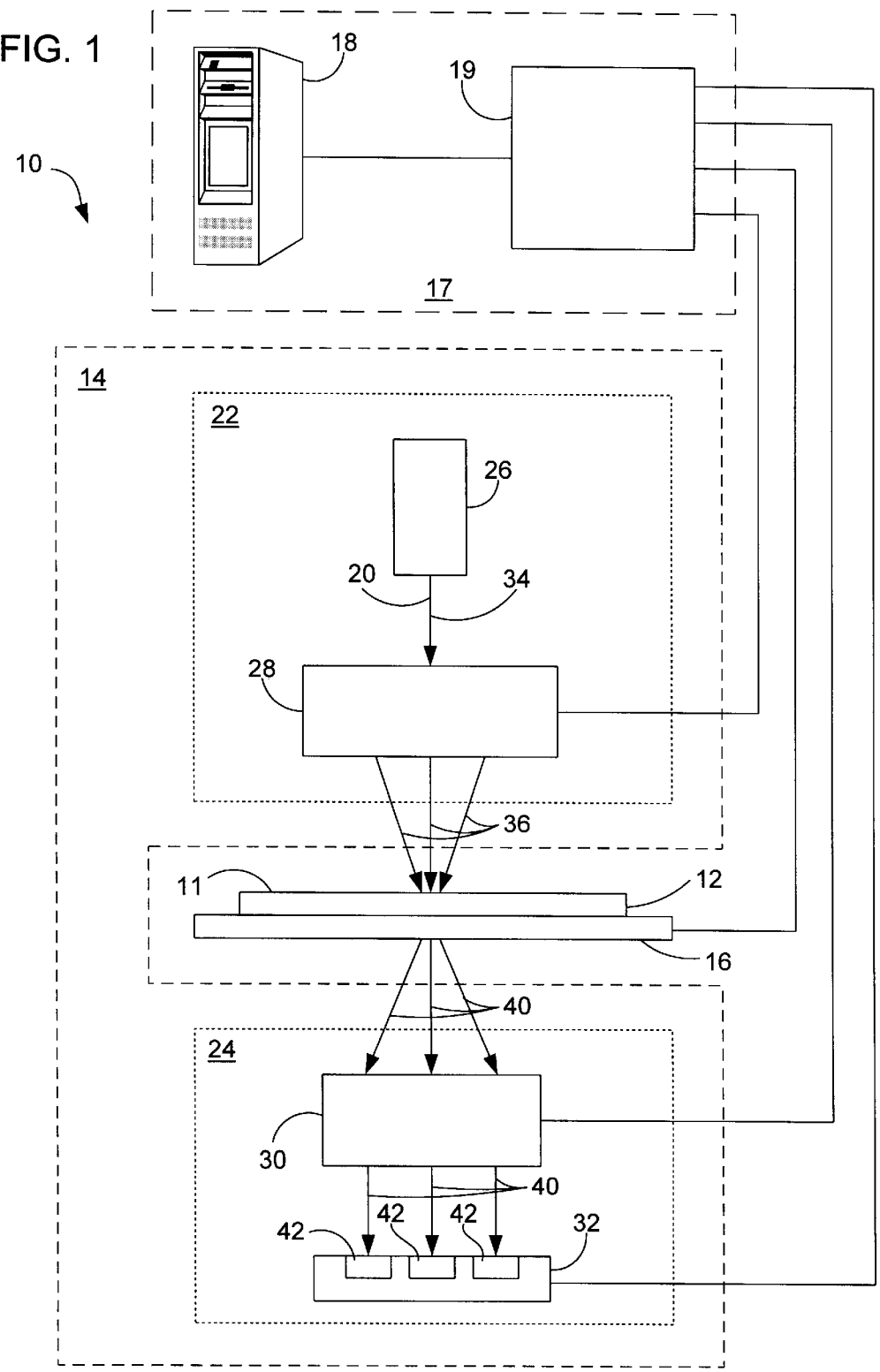
FIG. 1 is a simplified block diagram of an optical inspection system, in accordance with one embodiment of the present invention.

FIG. 1 is a simplified block diagram of an optical inspection system 10, in accordance with one embodiment of the present invention. The optical inspection system 10 is arranged for inspecting a surface 11 of a substrate 12. The dimensions of various components are exaggerated to better illustrate the optical components of this embodiment. As shown, the optical inspection system 10 includes an optical assembly 14, a stage 16, and a control system 17. The optical assembly 14 generally includes at least a first optical arrangement 22 and a second optical arrangement 24. In general terms, the first optical arrangement 22 generates two or more beams incident on the substrate, and the second optical arrangement 24 detects two or more beams emanating from the sample as a result of the two or more incident beams. The first and second optical arrangement may be arranged in suitable manner in relation to each other. For example, the second optical arrangement 24 and the first optical arrangement 22 may both be arranged over the substrate surface 11 so that reflected beams resulting from incident beams generated by the first optical arrangement 22 may be detected by the second optical arrangement 24.

In the illustrated embodiment, the first optical arrangement 22 is arranged for generating a plurality of scanning spots (not shown) along an optical axis 20. As should be appreciated, the scanning spots are used to scan the surface 11 of the substrate 12. On the other hand, the second optical arrangement 24 is arranged for collecting transmitted and/or reflected light that is produced by moving the scanning spots across the surface 11 of the substrate 12.

To elaborate further, the first optical arrangement 22 includes at least a light source 26 for emitting a light beam 34 and a first set of optical elements 28. The first set of optical elements 28 may be arranged to provide one or more optical capabilities including, but not limited to, separating the light beam 34 into a plurality of incident light beams 36, directing the plurality of incident light beams 36 to intersect with the surface 11 of the substrate 12, and focusing the plurality of incident light beams 36 to a plurality of scanning spots (not shown in FIG. 1) on the surface 11 of the substrate 12. The amount of first beams produced generally corresponds to the desired inspection speed. In one embodiment, the optical elements are arranged to separate the beam 34 into three incident light beams 36. By triplicating the beam, a wider scan is produced and therefore the resulting inspection speed is about three times faster than the speed produced for a non-triplicated single beam. Although only three light beams are shown, it should be understood that the number of separated light beams may vary according to the specific needs of each optical inspection system. For example, two beams may be used or four or more beams may be used. It should be noted, however, that the complexity of the optic elements is directly proportional to the number of beams produced.

Furthermore, the second optical arrangement 24 includes at least a second set of optical elements 30 and a light detecting arrangement 32. The second set of optical elements 30 are in the path of a plurality of collected light beams 40, which are formed after the plurality of incident light beams 36 intersect with the surface 11 of the substrate 12. The plurality of collected light beams 40 may result from transmitted light that passes through the substrate 12 and/or reflected light that is reflected off the surface 11 of the substrate 12. The second set of optical elements 30 are adapted for collecting the plurality of collected light beams 40 and for focusing the collected light beams 40 on the light detecting arrangement 32. The light detecting arrangement 32 is arranged for detecting the light intensity of the collected light beams 40, and more particularly for detecting changes in the intensity of light caused by the intersection of the plurality of incident light beams with the substrate. The light detecting arrangement 32 generally includes individual light detectors 42 that correspond to each of the second light beams 40. Furthermore, each of the detectors 42 is arranged for detecting the light intensity and for generating signals based on the detected light.

With regards to the stage 16, the stage 16 is arranged for moving the substrate 12 within a single plane (e.g., x & y directions) and relative to the optical axis 20, so that all or any selected part of the substrate surface 11 may be inspected by the scanning spots. In most embodiments, the stage 16 is arranged to move in a serpentine fashion. With regards to the control system 17, the control system 17 generally includes a control computer 18 and an electronic subsystem 19. Although not shown, the control system 17 may also include a keyboard for accepting operator inputs, a monitor for providing visual displays of the inspected substrate (e.g., defects), a database for storing reference information, and a recorder for recording the location of defects. As shown, the control computer 18 is coupled to the electronic subsystem 19 and the electronic subsystem 19 is coupled to various components of the optical inspection system 10, and more particularly to the stage 16 and the optical assembly 14 including the first optical arrangement 22 and the second optical arrangement 24. The control computer 18 may be arranged to act as an operator console and master controller of the system. That is, all system interfaces with an operator and the user's facilities may be made through the control computer 18. Commands may be issued to and status may be monitored from all other subsystems so as to facilitate completion of operator assigned tasks.

On the other hand, the electronics subsystem 19 may also be configured to interpret and execute the commands issued by control computer 18. The configuration may include capabilities for, but not limited to, digitizing the input from detectors, compensating these readings for variations in the incident light intensity, constructing a virtual image of the substrate surface based on the detected signals, detecting defects in the image and transferring the defect data to the control computer 18, accumulating the output of the interferometers used to track the stage 16, providing the drive for linear motors that move the stage 16 or components of the optical assembly 14, and monitoring sensors which indicate status. Control systems and stages are well know in the art and for the sake of brevity will not be discussed in greater detail. By way of example, a representative stage, as well as a representative controller may be found in U.S. Pat. No. 5,563,702, which is herein incorporated by reference. It should be understood, however, that this is not a limitation and that other suitable stages and control systems may be used.

As should be appreciated, the optical inspection system 10 can be arranged to perform several types of inspection, for example, transmitted light inspection, reflected light inspection and simultaneous reflected and transmitted inspection. In transmitted light inspection, light is incident on the substrate, a photomask for example, and the amount of light transmitted through the mask is detected. In reflected light inspection, the light reflecting from a surface of the substrate under test is measured. In addition to these defect detection operations, the system is also capable of performing line width measurement.

In most of the defect detection operations a comparison is made between two images. By way of example, the comparison may be implemented by the electronic subsystem 19 of FIG. 1. Broadly speaking, the detectors 42 generate scan signals, which are based on the measured light intensity, and send the scan signals to the electronic subsystem 19. The electronic subsystem 19, after receiving the scan signals, correspondingly compares the scan signals with reference signals, which are either stored in a database or determined in a current or previous scan.

More specifically, in die-to-die inspection mode, two areas of the substrate having identical features (dice) are compared with respect to each other and any substantial discrepancy is flagged as a defect. In the die-to-database inspection mode, a defect is detected by comparing the die under test with corresponding graphics information obtained from a computer aided database system from which the die was derived. In other defect detection operations, a comparison is made between two different modes of inspection. For example, in simultaneous reflected and transmitted inspection, a comparison is made between the light that is reflected off the surface of the substrate and light that is transmitted through the substrate. In this type of inspection the optical inspection system performs all of the inspection tasks using only the substrate to be inspected. That is, no comparisons are made between an adjacent die or a database.

Figure 2:
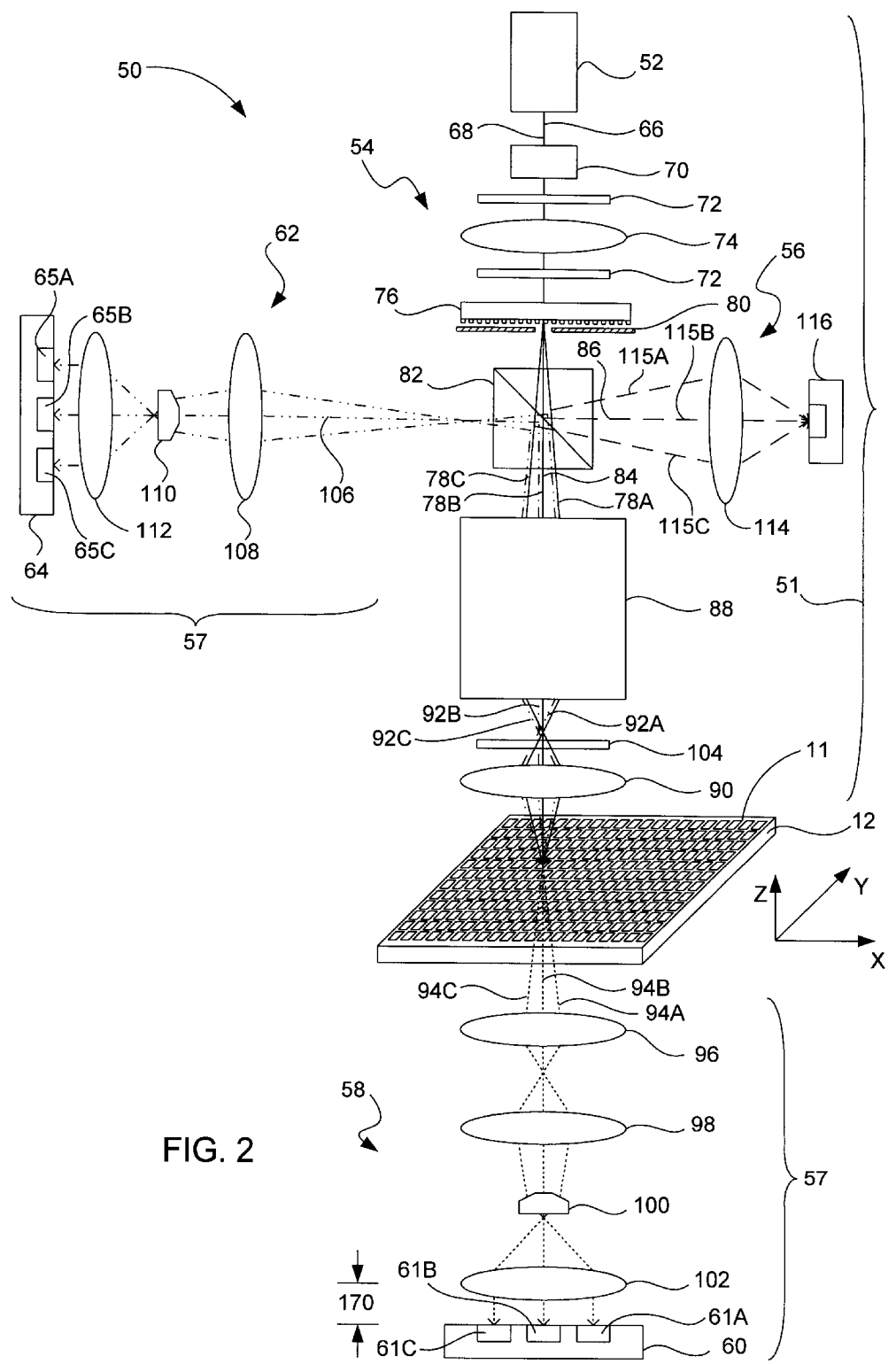
FIG. 2 is a detailed block diagram of an optical inspection system for inspecting the surface of a substrate, in accordance with one embodiment of the present invention.

FIG. 2 is a detailed block diagram of an optical assembly 50 for inspecting the surface 11 of the substrate 12, in accordance with one embodiment of the present invention. By way of example, the optical assembly 50 may be the optical assembly 14 as described in FIG. 1. The optical assembly 50 generally includes a first optical arrangement 51 and a second optical arrangement 57, both of which may respectively correspond to the first optical arrangement 22 and the second optical arrangement 24 of FIG. 1. As shown, the first optical arrangement 51 includes at least a light source 52, inspection optics 54, and reference optics 56, while the second optical arrangement 57 includes at least transmitted light optics 58, transmitted light detectors 60, reflected light optics 62, and reflected light detectors 64.

The light source 52 is arranged for emitting a light beam 66 along a first path 68. The light beam 66 emitted by the light source 52, first passes through an acousto optic device 70, which is arranged for deflecting and focusing the light beam. Although not shown, the acousto optic device 70 may include a pair of acouto-optic elements, which may be an acouto-optic prescanner and an acousto-optic scanner. These two elements deflect the light beam in the Y-direction and focus it in the Z-direction. By way of example, most acousto-optic devices operate by sending an RF signal to quartz or a crystal such as $TeO_2$. The signal causes a sound wave to travel through the crystal. Because of the travelling sound wave, the crystal becomes asymmetric, which causes the index of refraction to change throughout the crystal. This change causes incident beams to form a focused travelling spot which is deflected in an oscillatory fashion.

When the light beam 66 emerges from the acousto-optic device 70, it then passes through a pair of quarter wave plates 72 and a relay lens 74. The relay lens 74 is arranged to collimate the light beam 66. The collimated light beam 66 then continues on its path until it reaches a diffraction grating 76. The diffraction grating 76 is arranged for flaring out the light beam 66, and more particularly for separating the light beam 66 into three distinct beams, which are designated 78A, 78B and 78C. In other words, each of the beams are spatially distinguishable from one another (i.e., spatially distinct). In most cases, the spatially distinct beams 78A, 78B and 78C are also arranged to be equally spaced apart and have substantially equal light intensities.

Upon leaving the diffraction grating 76, the three beams 78A, 78B and 78C pass through an aperture 80 and then continue along path 68 until they reach a beam splitter cube 82. The beam splitter cube 82 (working with the quarter wave plates 72) is arranged to divide the beams into paths 84 and 86. Path 84 is used to distribute a first light portion of the beams to the substrate 12 and path 86 is used to distribute a second light portion of the beams to the reference optics 56. In most embodiments, most of the light is distributed to the substrate 12 along path 84 and a small percentage of the light is distributed to the reference optics 56 along path 86. It should be understood, however, that the percentage ratios may vary according to the specific design of each optical inspection system. In brief, the reference optics 56 include a reference collection lens 114 and a reference detector 116. The reference collection lens 114 is arranged to collect and direct the second portion of the beams, now designated 115A–C, on the reference detector 116. As should be appreciated, the reference detector 116 is arranged to measure the intensity of the light. Although not shown in FIG. 2, the reference detector 116 is generally coupled to an electronic subsystem such as the electronic subsystem 19 of FIG. 1 such that the data collected by the detector can be transferred to the control system for analysis. Reference optics are generally well known in the art and for the sake of brevity will not be discussed in detail.

The three beams 78A, 78B and 78C continuing along path 84 are received by a telescope 88. Although not shown, inside the telescope 88 there are a several lens elements that redirect and expand the light. In one embodiment, the telescope is part of a telescope system that includes a plurality of telescopes rotating on a turret. For example, three telescopes may be used. The purpose of these telescopes is to vary the size of the scanning spot on the substrate and thereby allow selection of the minimum detectable defect size. More particularly, each of the telescopes generally represents a different pixel size. As such, one telescope may generate a larger spot size making the inspection faster and less sensitive (e.g., low resolution), while another telescope may generate a smaller spot size making inspection slower and more sensitive (e.g., high resolution).

From the telescope 88, the beams 78A, 78B and 78C pass through an objective lens 90, which is arranged for focusing the beams 78A, 78B and 78C onto the surface 11 of the substrate 12. As the beams 78A–C intersect the surface 11 of the substrate 12 both reflected light beams 92A, 92B, and 92C and transmitted light beams 94A, 94B, and 94C may be generated. The transmitted light beams 94A, 94B, and 94C pass through the substrate 12, while the reflected light beams 92A, 92B, and 92C reflect off the surface 11 of the substrate 12. By way of example, the reflected light beams 92A, 92B, and 92C may reflect off of an opaque surfaces of the substrate, and the transmitted light beams 94A, 94B, and 94C may transmit through transparent areas of the substrate. The transmitted light beams 94 are collected by the transmitted light optics 58 and the reflected light beams 92 are collected by the reflected light optics 62.

With regards to the transmitted light optics 58, the transmitted light beams 94A, 94B, 94C, after passing through the substrate 12, are collected by a first transmitted lens 96 and focussed with the aid of a spherical aberration corrector lens 98 onto a transmitted prism 100. As shown, the prism 100 has a facet for each of the transmitted light beams 94A, 94B, 94C that are arranged for repositioning and bending the transmitted light beams 94A, 94B, 94C. In most cases, the prism 100 is used to separate the beams so that they each fall on a single detector in the transmitted light detector arrangement 60. As shown, the transmitted light detector arrangement 60 includes three distinct detectors 61A–C, and more particularly a first transmission detector 61A, a second transmission detector 61B, and a third transmission detector 61C. Accordingly, when the beams 94A–C leave the prism 100 they pass through a second transmitted lens 102, which individually focuses each of the separated beams 94A, 94B, 94C onto one of these detectors 61A–C. For example, beam 94A is focused onto transmission detector 61A; beam 94B is focused onto transmission detector 61B; and beam 94C is focused onto transmission detector 61C. As should be appreciated, each of the transmission detectors 61A, 61B, or 61C is arranged for measuring the intensity of the transmitted light.

With regards to the reflected light optics 62, the reflected light beams 92A, 92B, and 92C after reflecting off of the substrate 12 are collected by the objective lens 90, which then directs the beams 92A–C towards the telescope 88. Before reaching the telescope 88, the beams 92A–C also pass through a quarter wave plate 104. In general terms, the objective lens 90 and the telescope 88 manipulate the collected beams in a manner that is optically reverse in relation to how the incident beams are manipulated. That is, the objective lens 90 re-collimates the beams 92A, 92B, and 92C, and the telescope 88 reduces their size. When the beams 92A, 92B, and 92C leave the telescope 88, they continue along path 84 (backwards) until they reach the beam splitter cube 82. The beam splitter 82 is arranged to work with the quarter wave-plate 104 to direct the beams 92A, 92B, and 92C onto a path 106.

The beams 92A, 92B, and 92C continuing on path 106 are then collected by a first reflected lens 108, which focuses each of the beams 92A, 92B, and 92C onto a reflected prism 110, which includes a facet for each of the reflected light beams 92A–C. The reflected prism 110 is arranged for repositioning and bending the reflected light beams 92A, 92B, 92C. Similar to the transmitted prism 100, the reflected prism 110 is used to separate the beams so that they each fall on a single detector in the reflected light detector arrangement 64. As shown, the reflected light detector arrangement 64 includes three individually distinct detectors 65A–C, and more particularly a first reflected detector 65A, a second reflected detector 65B, and a third reflected detector 65C. Of course, each detector may be packaged separately or together. When the beams 92A–C leave the prism 110, they pass through a second reflected lens 112, which individually focuses each of the separated beams 92A, 92B, 92C onto one of these detectors 65A–C. For example, beam 92A is focused onto reflected detector 65A; beam 92B is focused onto reflected detector 65B; and beam 92C is focused onto reflected detector 65C. As should be appreciated, each of the reflected detectors 65A, 65B, or 65C is arranged for measuring the intensity of the reflected light.

There are a multiplicity of inspection modes that can be facilitated by the aforementioned optical assembly 50. By way of example, the optical assembly 50 can facilitate a transmitted light inspection mode, a reflected light inspection mode, and a simultaneous inspection mode. With regards to transmitted light inspection mode, transmission mode detection is typically used for defect detection on substrates such as conventional optical masks having transparent areas and opaque areas. As the light beams 94A–C scan the mask (or substrate 12), the light penetrates the mask at transparent points and is detected by the transmitted light detectors 61A–C, which are located behind the mask and which measure the light of each of the light beams 94AC collected by the transmitted light optics 58 including the first transmitted lens 96, the second transmitted lens 102, the spherical aberration lens 98, and the prism 100.

With regards to reflected light inspection mode, reflected light inspection can be performed on transparent or opaque substrates that contain image information in the form of chromium, developed photoresist or other features. Light reflected by the substrate 12 passes backwards along the same optical path as the inspection optics 54 but is then diverted by a polarizing beam splitter 82 into detectors 65A–C. More particularly, the first reflected lens 108, the prism 110 and the second reflected lens 112 project the light from the diverted light beams 92A–C onto the detectors 65A–C. Reflected light inspection may also be used to detect contamination on top of opaque substrate surfaces.

With regards to simultaneous inspection mode, both transmitted light and reflected light are utilized to determine the existence and/or type of a defect. The two measured values of the system are the intensity of the light beams 94A–C transmitted through the substrate 12 as sensed by transmitted light detectors 61A–C and the intensity of the reflected light beams 92A–C as detected by reflected light detectors 65A–C. Those two measured values can then be processed to determine the type of defect, if any, at a corresponding point on the substrate 12.

More particularly, simultaneous transmitted and reflected detection can disclose the existence of an opaque defect sensed by the transmitted detectors while the output of the reflected detectors can be used to disclose the type of defect. As an example, either a chrome dot or a particle on a substrate may both result in a low transmitted light indication from the transmission detectors, but a reflective chrome defect may result in a high reflected light indication and a particle may result in a lower reflected light indication from the same reflected light detectors. Accordingly, by using both reflected and transmitted detection one may locate a particle on top of chrome geometry which could not be done if only the reflected or transmitted characteristics of the defect was examined. In addition, one may determine signatures for certain types of defects, such as the ratio of their reflected and transmitted light intensities. This information can then be used to automatically classify defects.

By way of example, representative inspection modes including, reflected, transmitted and simultaneous reflected and transmitted modes, may be found in U.S. Pat, No. 5,563,702, which is herein incorporated by reference. It should be understood, however, that these modes are not a limitation and that other suitable modes may be used.

Figure 5:
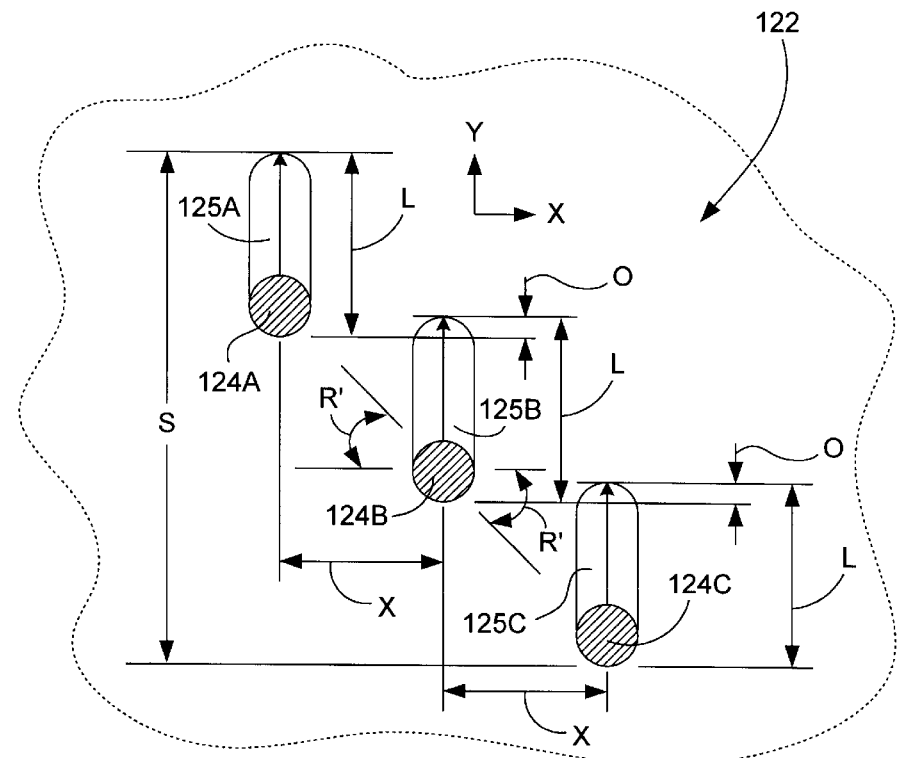
FIG. 5 is a detailed top view diagram of the scanning spot distribution produced by the inspection optics of FIGS. 3A–C, in accordance with one embodiment of the present invention.
Figure 8:
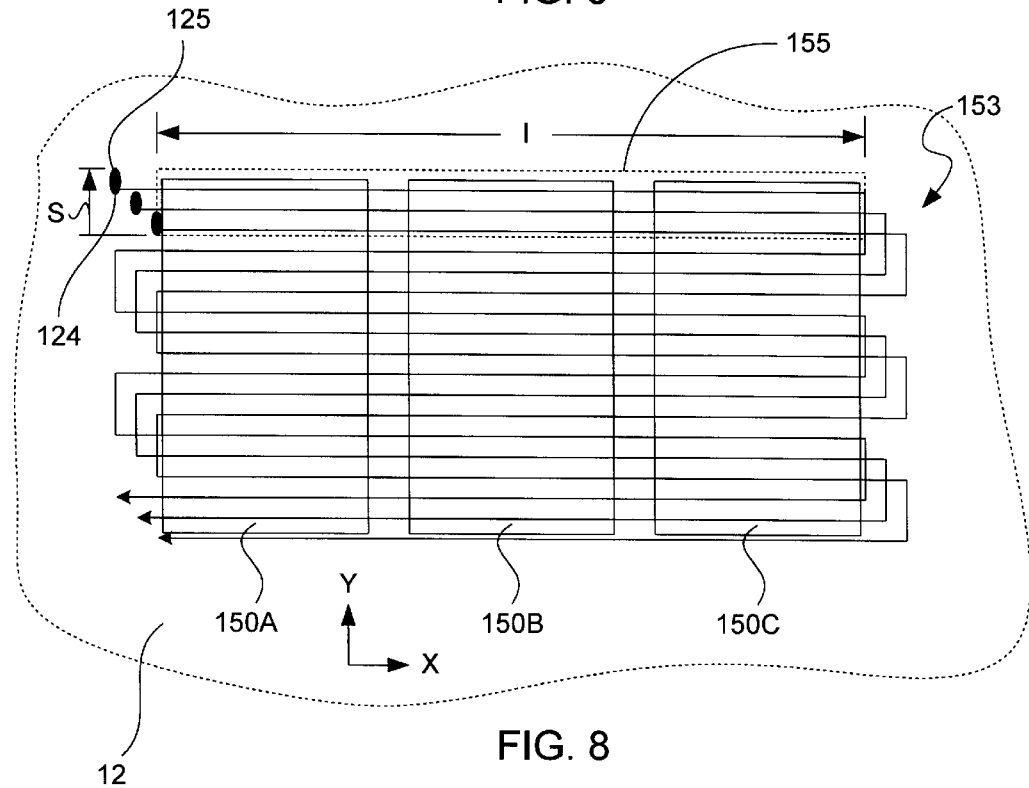
FIG. 8 is a top view illustration of a scanning spot distribution as it is moved over a substrate, in accordance with one embodiment of the present invention.
Figure 6:
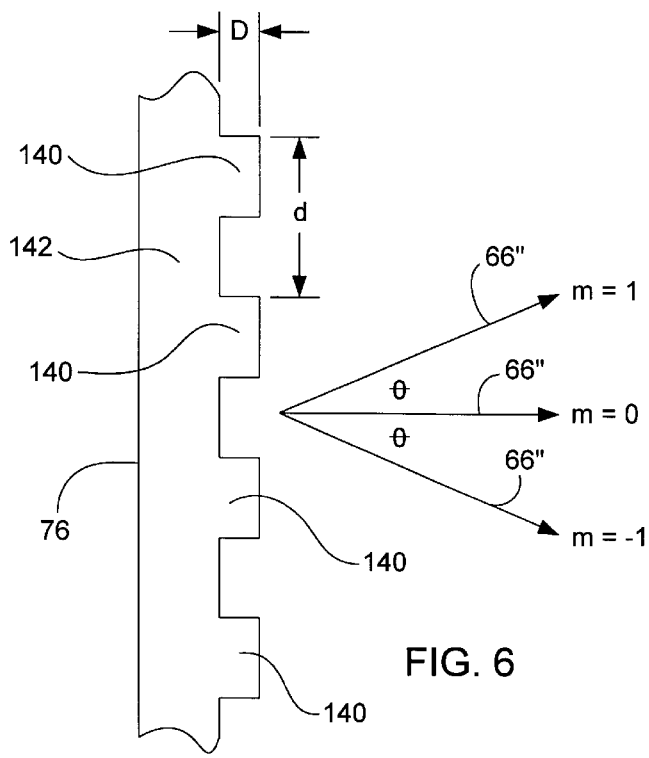
FIG. 6 is a side view diagram, in cross section, of a diffraction grating, in accordance with one embodiment of the present invention.

Referring now to FIGS. 3–8, the inspection optics 54 will be described in greater detail. In brief, FIGS. 3A–C are side view illustrations of the light source 52 and the inspection optics 54, as the light beams 78A–C are scanned across the surface 11 of the substrate 12, in accordance with one embodiment of the present invention. FIGS. 4A–C are top view illustrations of the scanning spots 124A–C produced by the inspection optics 54, also as the light beams 78A–C are scanned across the surface 11 of the substrate 12, in accordance with one embodiment of the present invention. Accordingly, FIG. 3A is associated with FIG. 4A; FIG. 3B is associated with FIG. 4B; and FIG. 3C is associated with FIG. 4C. Furthermore, FIG. 5 is a detailed top view diagram of the scanning spot distribution 122 produced by the inspection optics 54, in accordance with one embodiment of the present invention. FIG. 6 is a side view diagram, in cross section, of the diffraction grating 76, in accordance with one embodiment of the present invention. FIGS. 7A–B are top view diagrams of the diffraction grating 76, in accordance with one embodiment of the present invention. FIG. 8 is a top view illustration of the scanning spots 124A–C as they are moved across the substrate 12, in accordance with one embodiment of the present invention.

As shown in FIGS. 3 and 4, the light source 52 is configured to generate a single light beam 66 and the inspection optics 54 are configured to perform a variety of tasks associated with the single light beam 66 including, but not limited to, separating the single beam of light 66 into a plurality of light beams 78A–C, causing the plurality of light beams 78A–C to be deflected or swept over a small angle from one side (as shown in FIG. 3A) to the opposite side (as shown in FIG. 3C) of an optical axis 120, and focusing the deflected light beams 78A–C to scanning spots 124A–C on the surface 11 of the substrate 12 (as shown in FIGS. 4A–C). As should be appreciated, scanning spot 124A corresponds to light beam 78A; scanning spot 124B corresponds to light beam 78B; and scanning spot 124C corresponds to light beam 78C.

As shown in FIGS. 3A–C, the inspection optics 54 used to form the scanning spots 124A–C include an acousto-optic device 70, a relay lens 74, a diffraction grating 76, an aperture 80, a telescope 88, and an objective lens 90. As such, the light source 52 generates a light beam 66, which is made incident on the acousto-optice device 70. The acousto-optice device 70, in turn, deflects the light beam 66 in the Y-direction and relative to the optical axis 120. For ease of discussion, the deflected light beam is designated 66'. To elaborate further, the acousto-optic device 70 moves the beam 66 between reference point 126 and reference point 128. FIG. 3A shows the beam 66 after it has been deflected to reference point 126; FIG. 3B shows the beam 66 after it has been deflected to reference point 127 (which is between reference points 126 and 128); and FIG. 3C shows the beam 66 after it has been deflected to reference point 128. As should be appreciated, each of these sweep positions occurs at a different time in a given sweep. For example, FIG. 3A may show the beam at a first time, $T_1$; FIG. 3B may show the beam at a second time, $T_2$; and FIG. 3C may show the beam at a third time, $T_3$. Although, the sweeps are shown segmented in FIGS. 3A–C, it should be noted that the acousto-optic device typically operates at the speed of sound and as a result the sweep is almost instantaneous.

Furthermore, the deflected distance D, defined by reference points 126 and 128, generally corresponds to a scanning length L for each of the scanning spots 124A–C (as shown in FIGS. 4A & C). Moreover, the combination of each of these individual scans or stripes (e.g., distance L) results in a scanning swath S, which is the overall length of the three scans. As should be appreciated, the scanning swath S is about three times as large as an individual scan L, and therefore the scanning speed is about three times as fast. That is, the field size is larger and therefore more of the substrate is inspected for each scan, i.e., fewer turnarounds are needed with respect to the serpentine motion of the stage.

As shown in FIGS. 3A–C, when the deflected beam 66' emerges from the acousto-optic device 70 it is diverging towards the relay lens 74. As the deflected beam 66' passes through the relay lens 74, it is collimated such that diverging beam is turned into a collimated or parallel beam 66". Upon leaving the relay lens 74, the collimated beam 66" is made incident on the diffraction grating 76. The diffraction grating 76 correspondingly separates the collimated beam 66" into three distinct light beams 78A–C that are used to produce the scanning spot distribution 122 (e.g., spots 124A–C). The three beams 78A–C generally move together as a group when the acousto-optic device 70 deflects the light beam 66 between the reference points 126 and 128.

Referring to FIGS. 6 and 7, the diffraction grating 76 is generally formed by ruling equally spaced parallel lines or gratings 140 on a plate 142, which is formed from either glass or metal. Gratings ruled on metal plates are called reflective type gratings because their effects are viewed in reflected light rather than transmitted light. Conversely, gratings ruled on glass plates are called transmission type gratings because their effects are viewed in transmitted light rather than reflected light. By way of example, transmission type gratings include phase diffraction gratings, which have gratings etched into the glass plate and amplitude diffraction gratings, which have chrome gratings deposited on the glass plate. In phase gratings, the entire grating is formed of glass or quartz material, and therefore more light is transmitted through the grating. In amplitude gratings, the grating is formed from chrome, and therefore less light is transmitted through the diffraction grating, i.e., a portion of the light is blocked by the chrome gratings. In the illustrated embodiment, a phase diffraction grating is used over amplitude diffraction gratings because of its increased efficiency in transferring light. Although a phase diffraction grating is shown, it should be appreciated that both transmission type gratings (including amplitude gratings) and reflective type gratings may be used in the inspection optics. Furthermore, although only a single level grating is shown, it should be appreciated that multilevel gratings may also be used. In multilevel gratings, the rulings are stepped in levels with different depths.

To elaborate further, the diffraction grating 76 is arranged to split or scatter a single light beam into various diffraction orders and is generally controlled by the equation $2d\sin\theta = m\lambda$, where d is the grating spacing (i.e., the distance between rulings), m is the diffraction order (in integers), $\theta$ is the angle between diffraction orders, and $\lambda$ is the wavelength of the light incident on the grating. As shown in FIG. 6, the incident light beam 66" is split into diffraction orders m=1, m=0, m=−1 in order to generate the three distinct beams 78A–C. Furthermore, the depth, D, of the gratings is controlled to equalize the light beams light level so as to produce three equally intense light beams, i.e., the depth effects the efficiency of the transmitted light. It should be noted that the m=0 beam scans the same angular rate as the incident beam, but the m=1 and m=−1 beams scan at different and non-linear rates relative to the incident beam due to the sine term in the equation.

Referring back to FIGS. 3 and 4, each of the light beams 78A–C passes through the aperture 80 and is individually incident on the telescope 88 upon leaving the diffraction grating 76. The aperture 80 may be a metal plate with an opening for uniformly defining the image of the light beams. By way of example, the opening may be a circular opening that is arranged to change a square patch of light, which may be light traveling from the acousto-optic device 70 and relay lens 74, into a circular patch of light leaving the aperture 80. Furthermore, the telescope 88 serves to redirect and expand the light so as to result in more precise scanning spots 124A–C. Telescopes are generally well known in the art and for the sake of brevity will not be described in greater detail herein.

When the light beams 78A–C emerge from the telescope 88, they are individually incident on the objective lens 90. As shown in FIG. 3A–C, the light beams 78A–C are referred to as 78A'–C' after leaving the telescope 88. Moreover, when the light beams 78A'–C' travel between the telescope 88 and the objective lens 90 they pass through a pupil plane 130. By definition, a pupil plane is an image of the aperture 80. As shown in FIGS. 3A–C, the pupil plane 130 is the point where the beams 78A'–C' cross. Upon leaving the objective lens 90, each of the beams 78A'–C' is individually incident, and more particularly individually focussed on the surface 11 of the substrate 12. For ease of discussion, the light beams that have passed through the objective lens 90, and which are focussed, are referred to as 78A"–C". As a result of focusing the light beams 78A"–C" on the substrate 12, three spatially distinct scanning spots 124A–C are created on the substrate surface 11. The spatial separation of the spots 124A–C helps to ensure the proper collection of light at the detectors.

Although not shown, the objective lens 90 is typically connected to an Auto-Focus subsystem that is arranged for maintaining the focus of the beams as the beams are passed along the surface of the substrate. The Auto-Focus subsystem generally includes a servo or stepper motor that moves the objective lens up and down along the Z axis and relative to the substrate. As such, during the auto focus mode, the objective lens is arranged to move up and down to track the surface of the substrate so as to maintain focus. As should be appreciated, the motor is generally controlled by an electronic subsystem such as the electronic subsystem in FIG. 1. By way of example, a representative Auto-Focus subsystem may be found in Pat. No. 5,563,702, which is herein incorporated by reference. It should be understood, however, that this subsystem is not a limitation and that other suitable subsystems may be used.

In addition, the diffraction grating 76 may be configured to move in and out of the optical path 120 so as to allow the single beam 66 to continue through the inspection optics 54 without being separated into a plurality of beams. This may be desired for alignment and set-up modes, which are used to align the optics during an inspection set-up. This may also be desired for viewing the substrate in a live or review mode. The review mode is often used to characterize a known defect. Although not shown in FIG. 3, the diffraction grating may be coupled to a drive that is arranged for moving the diffraction grating in and out of the optical path. In most cases, the drive moves the diffraction grating orthogonal to the optical axis 120, for example, in the X or Y directions. By way of example, the drive may be a stepper motor. In order to control the drive, the drive is typically coupled to an electronic subsystem such as the electronic subsystem 19 of FIG. 1.

Referring now to FIG. 5, the scanning spot distribution 122 will be described in greater detail. As shown, the scanning spot distribution 122 includes offset and staggered scanning spots 124A–C, each of which has a scanning length L that forms a scanning stripe 125A–C in the Y-direction. Correspondingly, the combination of each of the scanning stripes 125A–C forms an overall scanning swath, S. Furthermore, the scanning spots 124A–C are spatially separated relative to one another to isolate the different scans or stripes 125A–C. By spatial separation, it is meant that each of the spots are isolated from other spots in the distribution such that they do not cover each other during a scan. As should be appreciated, it would be difficult to collect the light on the three individual detectors if the spots were not isolated in this manner.

To elaborate further, the scanning spots 124A–C are offset (or staggered) in both the X and Y directions. In the Y direction, the spots are offset by approximately the distance L, and more particularly the distance L less an overlap portion O. The overlap portion, O, is used to ensure that the scanning swath, S, is scanned without missing any areas therebetween. In the X direction, the spots are offset by a distance X. The distance L, O and X may vary according to the specific needs of each inspection system.

Figure 7A:
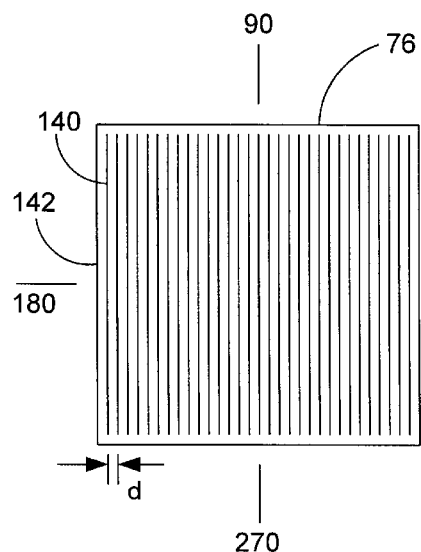
FIGS. 7A–B are top view diagrams of a diffraction grating, in accordance with one embodiment of the present invention.
Figure 7B:
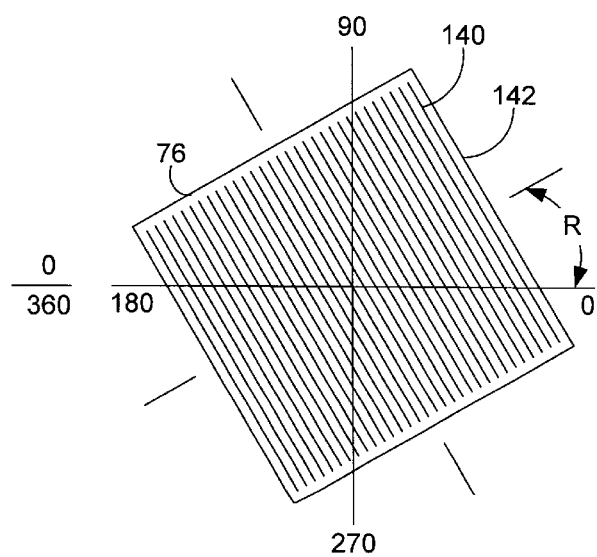
Figure 9:
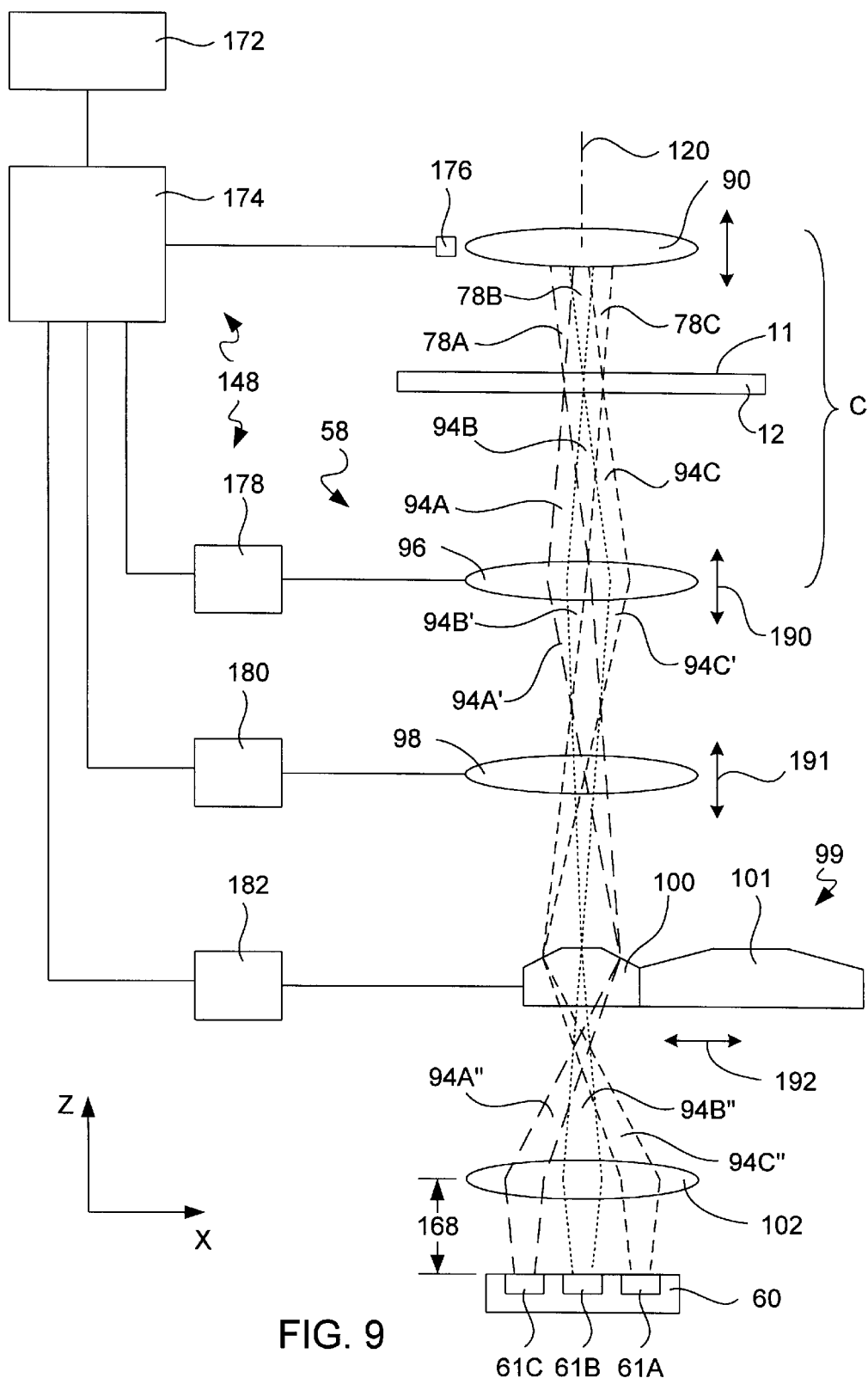
FIG. 9 is a side view illustration of the transmitted light optics and the transmitted light detector arrangement of FIG. 3, in accordance with one embodiment of the present invention.

In accordance with one embodiment of the present invention, and referring to FIGS. 7–9, the diffraction grating 76 is arranged to control both the overlap, O, and separation, X, of the scanning spots 124A–C. This can be accomplished by adjusting the grating spacing, d (as shown in FIGS. 6 & 7), and the rotation R of the diffraction grating 76 about the optical axis 120 (as shown in FIGS. 7A & B). FIG. 7A shows the diffraction grating before rotation and FIG. 7B shows the diffraction grating after rotation. As should be appreciated, both the grating spacing, d, and the rotation, R, effect the position of the scanning spots 124A–C. The grating spacing, d, causes separation between spots, while the rotation, R, causes the outside scanning spots to be rotated about the optical axis 120 such that they are spatially separated in both the X and Y directions (shown in FIG. 5 as R'). For the most part, a smaller grating spacing, d, generally produces a larger separation. Furthermore, the spots rotate about the axis (and about the center spot) at about the same angle as the diffraction grating is rotated about the axis. It is generally believed that if the diffraction grating is not rotated, then the scanning spots, although separated, may be too close to detect at the detectors.

Referring now to FIG. 8, a top view of the scanning spots 124A–C/stripes 125A–C, as they are moved across the substrate 12 will be disclosed, in accordance with one embodiment of the present invention. By way of example, the substrate 12 may be a photomask, reticle or wafer. As mentioned, the beam sweep or swath, S, is in a direction such that, after passing through the inspection optics, it is directed parallel to the Y-axis as viewed at the substrate 12. As the beams are swept, the stage (not shown in FIG. 8) carrying the substrate 12 under test is caused to move back and forth in the direction of the X-axis, for an inspection length I, while being incremented in the Y-direction at the end of each traverse so that the scanning spots 124A–C are caused to sweep along a serpentine path 153 across a predetermined area of the substrate 12. The predetermined area may correspond to a single identified sub area, a plurality of identified substrate sub areas (such as individual dice in the case of a photomask) or the entire substrate.

Prior to starting the inspection operation, the operator generally aligns the substrate in the proper orientation and defines the area to be inspected. The inspection area may be defined using the control computer of FIG. 1. In FIG. 8, the inspection area corresponds to three dice of a photomask respectively designated 150A, 150B, and 150C. In this manner, the surface area of the dice 150A–C are swept in a series of contiguous swaths, S, by the scanning spots 124A–C. As shown, each sweep in the X-direction produces an inspection area 155, which is the product of the swath, S, and the inspection length, I. The swath, S, may be overlapped at each traverse (in the Y-direction) so as to ensure that the entire inspection area is scanned without missing any areas therebetween. Accordingly, the field size or swath is larger and therefore more of the substrate is inspected for each scan, and as a result there tends to be fewer turnarounds. By way of example, by using three beams the inspection speed is approximately tripled.

By way of example, in a die to die comparison mode, the inspection of the substrate 12 ordinarily starts at the upper left hand corner of the first die 150A and follows the serpentine pattern 153. As the stage slowly moves in the X direction, the laser beams rapidly sweep in the Y-direction. In this manner, a swath S is scanned and the digitized output of the detectors is stored in, for example, the electronics subsystem 19 of FIG. 1. In the case of a transparent or partially transparent substrate, detection of the image is accomplished by the transmission detectors 61. The light reflected from the substrate is detected by a reflected light detectors 65. As such, when the scan reaches the right boundary of the care area of the first die 150A, image data derived from die 150A (left to right) is stored in subsystem 19. Correspondingly, when the scan reaches the right boundary of the second die 150B, image data derived from die 150A, which is now stored in subsystem 19, is compared with the data derived from die 150B. Any substantial difference is designated a defect. In a similar manner, the data from die 150C is also compared with the data derived from die 150B or 150A. When the scanning process reaches the right boundary of the die 150C, the stage is moved in the Y-direction an amount slightly less than the swath width and the stage starts a return trace in the X-direction. In this manner the care areas of the dice are traversed by the serpentine motion.

Although only the die to die inspection mode is described, it should be noted that this is not a limitation and that a die-to-database inspection or simultaneous inspection may also be performed. The die to database inspection is similar to die-to-die inspection except that the die is compared to a simulated image generated by the control system.

Furthermore, the system can be arranged for sampling the amplitude of the plurality of scan signals at precise intervals. The sampled scan signals combined with precise control of the stage motion and other factors are used to construct a virtual image of the pattern surface of the substrate. The sampling rate of each of the plurality of scans can be varied to compensate for the different and non-linear scan rates of the individual scans caused by the diffraction grating. The system is also capable of measuring the mentioned scan rate variations and automatically calibrating the required sample rate corrections. Sampling is generally well known in the art and for the sake of brevity will not be discussed in greater detail.

Figure 10:
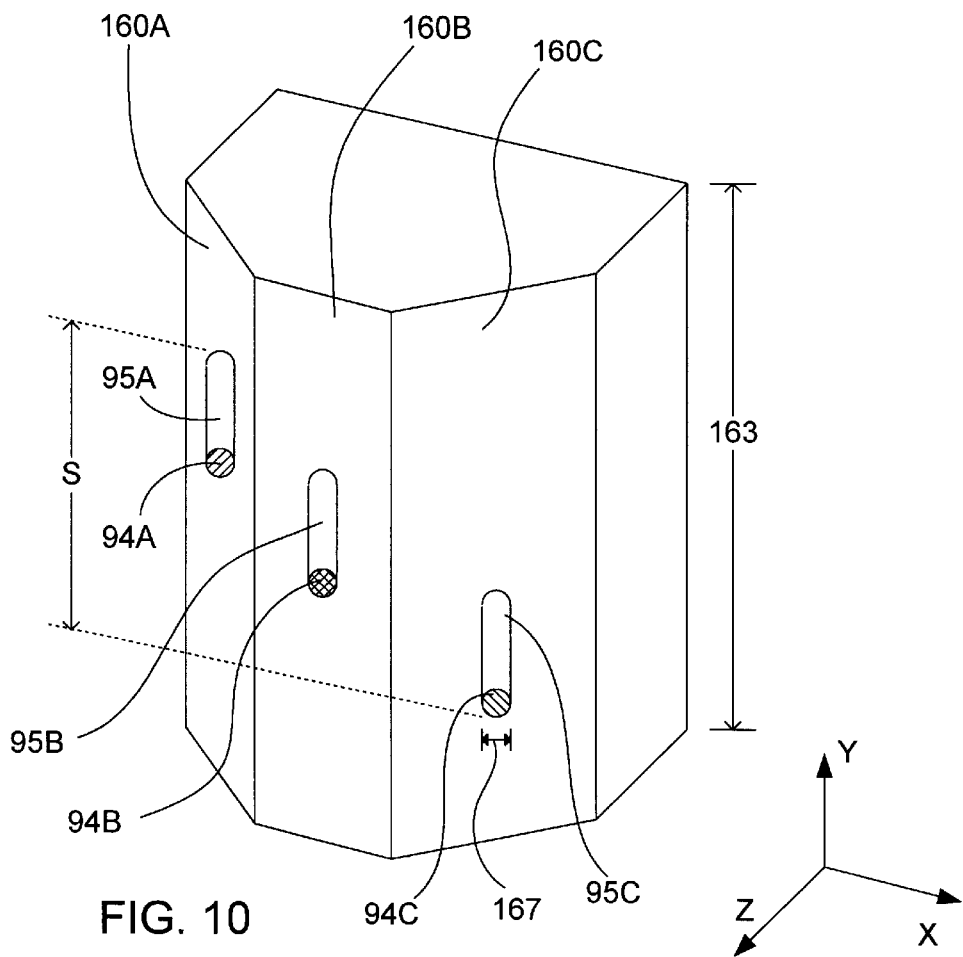
FIG. 10 is a detailed perspective diagram of a prism that can be used in either the transmitted light optics or reflected light optics, in accordance with one embodiment of the present invention.
Figure 11:
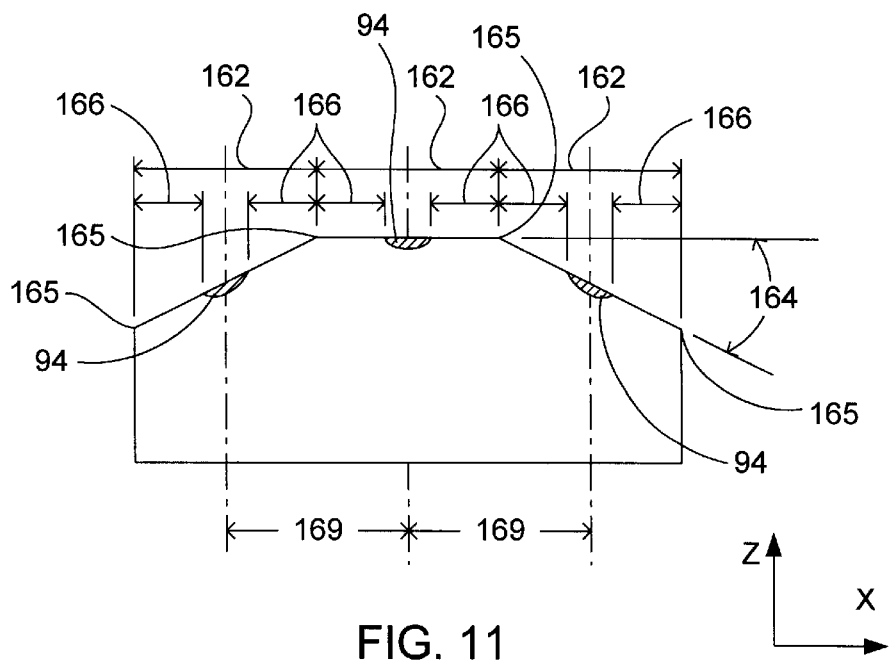
FIG. 11 is a side view diagram, in cross section, of a prism that can be used in either the transmitted light optics or reflected light optics, in accordance with one embodiment of the present invention.
Figure 12A:
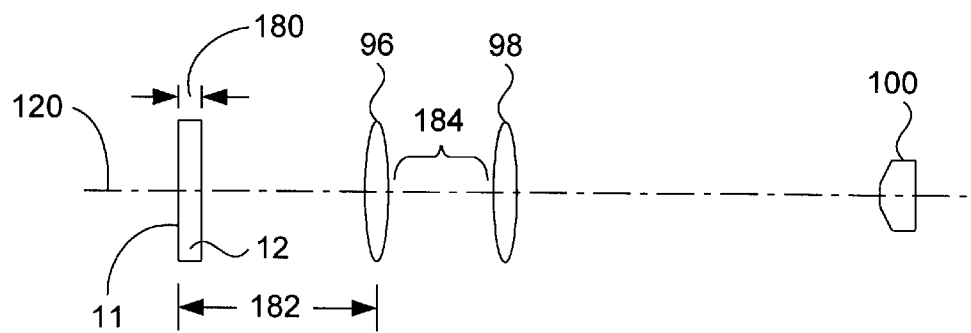
FIGS. 12A–C is a side view diagram illustrating the various positions of the first transmitted lens and the objective lens, in accordance with one embodiment of the present invention.
Figure 12B:
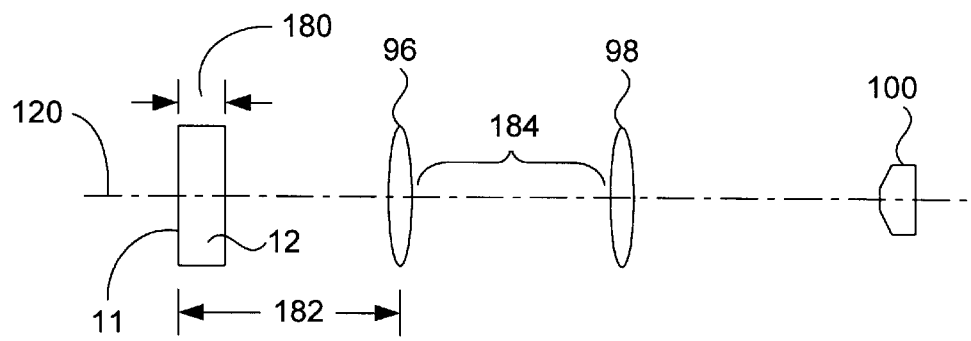
Figure 12C:
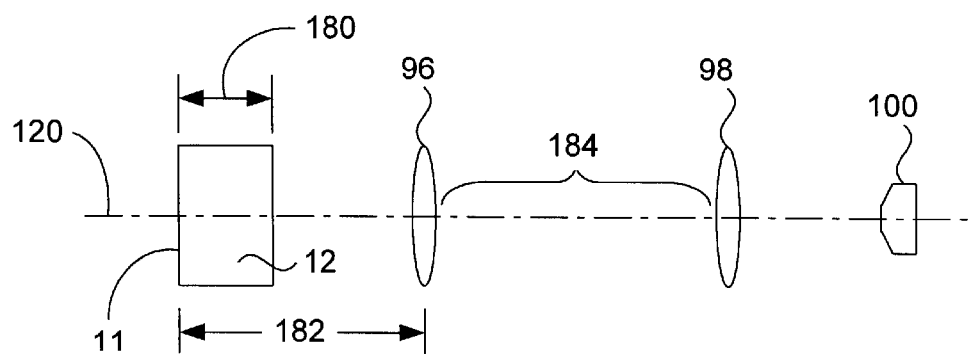
Figure 13:
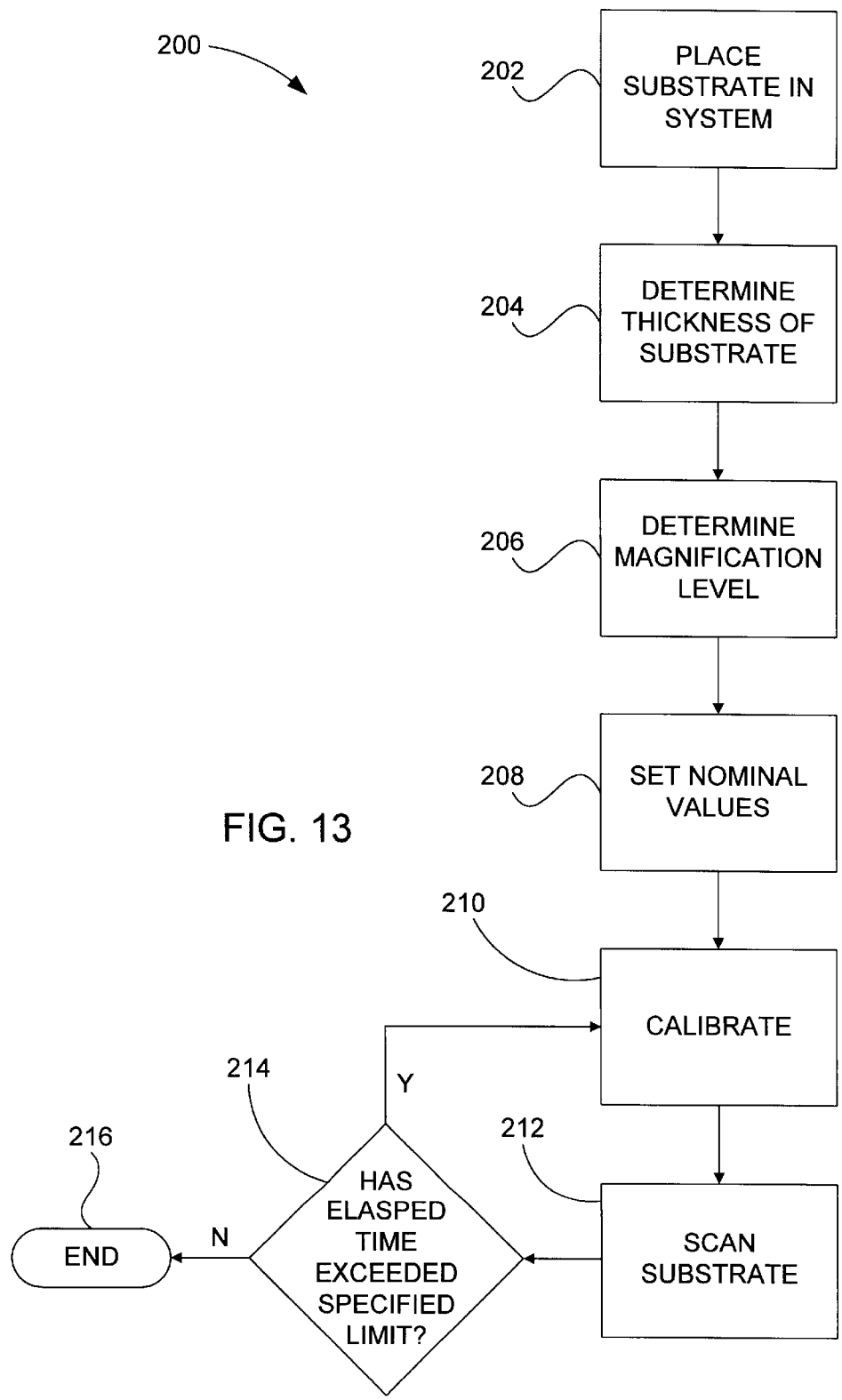
FIG. 13 is a flow diagram of an inspection set-up procedure, in accordance with one embodiment of the present invention.

Referring now to FIGS. 9–13, the transmitted light optics 58 will be described in greater detail. In brief, FIG. 9 is a side view illustration of the transmitted light optics 58 and the transmitted light detector arrangement 60. FIG. 10 is a detailed perspective diagram of the prism 100, in accordance with one embodiment of the present invention. FIG. 11 is a side view diagram, in cross section, of the prism 100, in accordance with one embodiment of the present invention. FIGS. 12A–C are side view diagrams illustrating the various positions of the first transmitted lens and spherical correction lens, in accordance with one embodiment of the present invention. FIG. 13 is a flow diagram of the transmitted optics set-up, in accordance with one embodiment of the present invention.

Referring first to FIG. 9, the transmitted light optics 58 are configured to receive a plurality of transmitted light beams 94A–C and the transmitted light detector arrangement 60 is configured to detect the light intensity of each of the plurality of transmitted beams 94A–C. More particularly, the transmitted light optics 58 are configured to perform a variety of tasks associated with the transmitted beams 94A–C including, but not limited to, collecting the transmitted light 94A–C, maintaining beam separation, and focusing the separated beams onto individual light detectors 61A–C of the transmitted light detector arrangement 60. As mentioned, prior to receiving the transmitted light beams 94A–C, the focused light beams 78A–C produced by the inspection optics 54 are made incident on the surface of a transmissive substrate. At least a portion of the incident light beams 78A–C are transmitted through the substrate 12 as transmitted light beams 94A–C to the transmitted light optics 58. The diagram is shown in the X & Z directions such that the Y direction is coming out of (or into) the page.

As shown in FIG. 9, the transmitted light optics 58 used to receive the transmitted light beams 94A–C include a first transmitted lens 96, a spherical aberration correction lens 98, a prism 100, and a second transmitted lens 102. The first transmitted lens 96 collects the diverging transmitted light beams 94A–C and along with the spherical aberration correction lens 98 focuses the transmitted light beams 94A–C onto the prism 100. The first transmitted lens 96 and the spherical aberration correction lens 98 work as a unit to produce well-defined spots on the first faceted prism 100. Focussed and well-defined spots at the prism 100 serve to reduce spot overlapping (i.e., beam intersects two facets), which tends to cause unwanted cross talk. As should be appreciated, cross talk may lead to erroneous signals, which may lead to inspection failure. In one embodiment, an automatic collection optics subsystem 148 is used to maintain focus on the prism 100. The automatic collection optics subsystem 148 maintains focus on the prism 100 by controlling the movement of the first transmitted lens 96, the spherical aberration correction lens 98, and the prism 100. The automatic collection optics subsystem 148 will be described in greater detail below. Furthermore, although not shown in FIG. 9, a third lens, positioned between the spherical aberration correction lens 98 and the prism 100, may be used help image quality at the prism 100.

To elaborate further, when the transmitted light beams 94A–C leave the substrate 12, they are bent by the first transmitted lens 96 towards the prism 100. For ease of discussion, the bent beams are designated 94 A'–C'. As the bent beams pass through the spherical aberration lens 98, they are bent further, although not much further, by the spherical aberration lens 98 towards the prism 100. As shown, the beams pass through a pupil plane 130 while travelling between the lenses 96 and 98. Upon leaving the spherical aberration lens 98, each of the bent beams 94 A'–C' are individually incident on an individual facet of the prism 100. As should be appreciated, the prism 100 is generally located at an image plane because that is where the beams are distinct and isolated from each other. If the prism is positioned anywhere else, the beams may overlap and cause errors in inspection. Furthermore, the prism 100 correspondingly bends and separates the light beams, now designated 94A"–C", such that they are separately directed towards one of the three individual detectors 61A–C. As should be appreciated, the prism 100 is used to ensure that each of the beams goes to an individual detector rather than all going to one detector.

In one embodiment, a prism system 99 having a plurality of prisms (shown here as prism 100 and prism 101) is used to accommodate the magnification range produced by the telescope of the inspection optics. For example, at certain magnifications the scans can be very large, and therefore a larger prism is needed to effectively separate the scans without cross talk. In one implementation, therefore, the prism 100 is a high resolution prism (e.g., small scan) and the prism 101 is a low resolution prism (e.g., large scan). Each of the prisms 100 and 101 is arranged to move in and out of the optical path 120 so as to adjust for different telescope magnifications.

Furthermore, both of the prisms 100 and 101 may be configured to move out of the optical path 120 for the same reasons as the diffraction grating 76, i.e., when only one beam is needed. As such, when the prisms are moved out of the optical path, a single beam is allowed to continue through the transmitted optics 58 without being separated. This may be desired for alignment and set-up modes, which are used to align the optics during an inspection set-up. This may also be desired for viewing the substrate 12 in a live or review mode. The review mode is often used to characterize a known defect.

Referring now to FIGS. 10 & 11, the prisms will be described in detail. Each prism includes three facets 160A, 160B, and 160C, which respectfully correspond to each of the transmitted light beams 94A–C (shown as spots on each of the facets). The first facet 160A corresponds to beam 94A; the second facet 160B corresponds to beam 94B; and the third facet corresponds to beam 94C. Furthermore, during a beam sweep each of the beams 94A–C forms a scan 95A–C in the Y direction on the surface of their corresponding facets 160A–C. Although only three facets are shown, it should be understood that the amount of facets corresponds to the amount of beams and therefore if more or less beams are used then the amount of facets will change accordingly.

To elaborate further, each of the facets are configured with a facet width 162, a facet length 163, and a facet angle 164. The facet widths 162 are defined by facet edges 165. The facet widths 162 are configured to provide a sufficient amount of tolerance 166 between the facet edges 165 and the edges of the spots 94 in order to maintain proper beam separation. As should be appreciated, if the tolerance 166 is too small or too large, on either side of the spot, then the beams may drift over the facet edge and into an adjacent facet or off of the facet all together. This type of drift may lead to alignment errors, out of focus errors, and cross talk errors. In most cases, the facet widths are selected relative to the size of the spots (spot size is designated 167) being used to scan the substrate in order to maintain an appropriate tolerance. For instance, when a larger spot size is used, i.e., low resolution, the facet width is arranged to be correspondingly larger, and when a smaller spot size is used, i.e., high resolution, the facet width is arranged to be correspondingly smaller. Furthermore, the facet length 163 is configured to provide a sufficient distance for scanning. That is, the facet length 163 is arranged to be greater than the swath height, S.

With regards to the facet angle 164, the facet angle 164 is arranged to direct the beams towards one of the detectors of the detector arrangement. As should be appreciated, the focal length (shown as 168 in FIG. 10) of the second lens and the facet angle 164 work together to get the desired beam separation at the detector plane. It is generally believed that for a given detector separation (shown as 170 in FIG. 9) and a given detector size (not shown), a larger facet angle, which produces a larger separation, needs a smaller focal length, and conversely, a smaller facet angle, which produces a smaller separation, needs a larger focal length. As such, when the facet angle is adjusted, so is the focal length of the lens.

Referring back to FIG. 9, after the separated light beams 94A"–C" pass through the prism 100, they pass through the second transmitted lens 102, which is arranged for focusing the separated beams on the detectors 61A–C of the transmitted detector arrangement 60. Upon leaving the second transmitted lens 102, the beams are made incident on the individual detectors 61A–C. As discussed, the second transmitted lens 102 focuses each of the beams 94A, 94B, 94C on a single respective detector. For example, beam 94A is focused onto transmission detector 61A; beam 94B is focused onto transmission detector 61B; and beam 94C is focused onto transmission detector 61C. As should be appreciated, each of the transmission detectors 61A, 61B, and 61C is arranged for measuring the intensity of the transmitted light. By way of example, the three detectors may be individually packaged chips or may be part of a single chip package (as shown). It should be noted, however, that the single chip package has the advantage of allowing closer packed detectors that allow for shallower incident angles.

Referring now to the collection subsystem 148, the collection subsystem 148 is used to adjust the positions of the first transmitted lens 96, the spherical aberration correction lens 98, and the prism 100 in order to properly focus and align the beams 94A–C on the prism 100. As mentioned, if the beams 94A–C are not focussed and/or aligned on the prism 100, then the beams 94A–C may not achieve proper separation or they may overlap one another. Improper separation and/or overlapping may cause erroneous inspections.

The collection subsystem 148 generally includes a system software element 172, a control interface 174, an objective position sensor 176, a first transmitted lens drive 178, a spherical aberration correction lens drive 180, and a prism drive 182. The system software element 172 may be arranged to act as the master controller of the subsystem, and may be implemented on a control computer such as the one described in FIG. 1. The system software element 172 is coupled to the control interface 174, which is configured to distribute and receive signals to and from the drives and sensors. The control interface 174 may be implemented in an electronic subsystem such as the one described in FIG. 1. Furthermore, the control interface 174 is coupled to the objective position sensor 176, the first transmitted drive 178, the spherical aberration correction lens drive 180, and the prism drive 182.

In brief, the objective position sensor 176 is arranged for monitoring the position of the objective lens 90, for example, when the objective lens 90 is moved along the optical axis to stay in focus with the substrate (Auto-Focus). The first transmitted drive 178 is arranged for moving the first transmitted 96 along the optical axis 120, and more particularly in the Z direction (as shown by arrow 190). The spherical aberration correction lens drive 180 is arranged for moving the spherical aberration lens 98 along the optical axis 120, and more particularly in the Z direction (as shown by arrow 191). The prism drive 182 is arranged for moving the prisms 100 and 101 orthogonal to the optical axis 120, and more particularly in the X direction (as shown by arrow 192). By way of example, all of the drives may include a motorized linear actuator for driving the movements of the aforementioned elements. Motorized actuators are well known in the art and for the sake of brevity will not be discussed in detail.

There are typically several conditions involved in focusing and alignment. A first condition includes setting a nominal position for the first transmitted lens 96, the spherical aberration correction lens 98, and the prism 100 for a predetermined substrate thickness and light magnification (e.g., telescope). As should be appreciated, different substrate thickness', as well as different magnifications, require different optical positions because of how they effect the transmitted light. For example, for a given optical position, i.e., the optics remain stationary, a change in substrate thickness (for example, from a ¼ in. substrate to a 90 mil substrate) tends to shift the position of the image plane and therefore the light at the prism tends to be out of focus. In addition, for a given optical position, a change in magnification tends to cause a change in beam separation and placement and therefore the light at the prism tends to overlap.

Accordingly, once the substrate size and magnification level is determined, the collection subsystem 148 moves the first transmitted lens 96, the spherical aberration correction lens 98, and one of the prisms 100, 101 to a pre-determined nominal value. In effect, the software element 172 via a control computer sends position information to the control interface 174, which then sends a movement signal to the first transmitted lens drive 178, the spherical aberration correction lens drive 180 and the prism drive 182 to move their respective optics according to the pre-determined nominal values. In general, for thicker substrates the lenses are moved away from the patterned surface of the substrate, while for thinner substrates the lenses are moved closer to the pattern surface of the substrate. Although they both move, it should be noted that the spherical aberration lens moves a larger distance than the first transmitted lens. Additionally, for larger spot sizes (or large pixel sizes), a larger prism, i.e., prism 101, is moved into the optical path, and for smaller spot sizes (or small pixel sizes), a smaller prism, i.e., prism 100, is moved into the optical path.

FIGS. 12A–C are exemplary diagrams illustrating the nominal positions for various substrate thickness.' In these figures, the thickness of the substrate is designated 180, the distance between the first transmitted lens 96 and the patterned surface 11 of the substrate 12 is designated 182, and the distance between the first transmitted lens 96 and the spherical aberration correction lens 98 is designated 184. As shown, the distances 182 and 184 are directly proportional to the thickness 180 of the substrate. That is, the distances 182 and 184 are smaller for thin substrates (as shown in FIG. 12C) and larger for thick substrates (as shown in FIG. 12A). Also as shown, the lower collection lens is moved a small distance relative to the distance moved by the spherical aberration lens.

Furthermore, and referring back to FIG. 9, a second condition includes calibrating the positions of the first transmitted lens 96 and the prism 100. Calibrating is a fine tuning process that generally aligns and focuses the optics. Calibration steps are typically conducted on every substrate to be inspected, and sometimes these steps are periodically repeated during the inspection process for long inspection runs. With respect to the prism 100, the prism is calibrated to find the best position of the prism orthogonal to the optical axis 120. For example, the prism 100 may be calibrated to center the incident beams on each of the facets 160A–C (as shown by the center to center distance 169 in FIG. 11). With respect to the first transmitted lens 96, the lens is calibrated to find the best position of the lens along the optical axis 120. For example, the lens position may be calibrated so as to focus the incident beams on each of the facets 160A–C. If the prism 100 and the first transmitted lens 96 are not aligned and focused properly, then there may be very little tolerance for the incident beams during inspection. As should be appreciated, a small tolerance may lead to light beam cross talk or improper beam separation. By way of example, thermal changes may effect the position of the lenses and as a result the beams may begin to cross over to an adjacent facet. In some cases, the calibration step includes measuring the amount of cross talk at the transmitted light detectors and moving the first transmitted lens and prism relative to their preset nominal values so as to minimize the amount of cross talk. The movement of the lens and prism are implemented through the control interface 174, which sends a signal to their respective drives to move accordingly. In most cases, these calibrations are done automatically by the control system 17, and as a result, no actions, instructions or information are required for the operator performing the inspection.

Also, the pattern surface may be slightly sloped or tilted, and, therefore, a third condition includes tracking the position of the first transmitted lens 96 relative to the position of the patterned surface 11 of the substrate 12 so as to maintain focus throughout the inspection. There are many ways to implement tracking. In one embodiment, tracking is implemented by moving the first transmitted lens 96 relative to the objective lens 90. As discussed above, during an inspection, the objective lens 90 is arranged to stay in focus with the substrate 12 by moving up and down along the optical axis 120 (in the Z direction). Accordingly, the objective lens movement can be used to also track the first transmitted lens 96. In this embodiment, a distance C between the first transmitted lens 96 and the objective lens 90 is held approximately constant. As such, when the objective lens 90 moves a focus distance z, for example, the first transmitted lens also moves a distance z. The distance C is based on the calibrated position of the first transmitted lens 96. In order to implement tracking, the objective position sensor 176 detects the position of the objective lens 90, and correspondingly sends a signal to the control interface 174, which then sends a signal to the first transmitted lens drive 178 to move the first transmitted lens 96 accordingly. Although only one embodiment of tracking is described, it should be noted that this is not a limitation and that other tracking methods may be used. For example, the first transmitted lens could also track the surface of the substrate directly without using the objective lens as a reference.

To elaborate further, FIG. 13 is a flow diagram of an inspection set-up procedure 200, in accordance with one embodiment of the invention. In operation 202, the substrate is initially placed into the inspection system, for example, the inspection system 10 as shown in FIG. 1. In most cases, this operation includes positioning the substrate on the stage 16. After the substrate is placed in the system and on the stage (operation 202), the thickness of the substrate is determined in operation 204. Determining the thickness of the substrate is generally well known in the art and for the sake of brevity will not be discussed in detail. After or during operation 204, the desired magnification level for the telescope is set in operation 206. The magnification level is generally chosen by the operator implementing the set-up. If the operator desires greater sensitivity then a high magnification level is typically chosen. Conversely, if the operator desires greater scanning speeds then a low magnification level is typically chosen.

Following operation 206, the position of the transmitted light optics are set at nominal values in operation 208. As mentioned, the transmitted optics with nominal values include the first transmitted lens 96, the spherical aberration correction lens 98 and the prism 100. The nominal values are generally selected by the system software and generally depend on the thickness of the substrate and the magnification level of the telescope. In most cases, the system software knows the state of the thickness and magnification and therefore it signals the interface to move the optics accordingly. By way of example, if the system software selected a program for highest magnification, and a ¼" substrate, then the first transmitted lens 96 and the spherical aberration correction lens 98 would move to a nominal ¼" substrate position. The appropriate prism is then moved to a nominal position for the high magnification inspection.

After the nominal values are set in operation 208, the transmitted light optics are calibrated in operation 210. The transmitted light optics that are calibrated include the first transmitted lens 96 and the prism 100. The calibration sequence generally includes collecting light values at the detectors 61A–C, analyzing the collected light values at the control interface 174, calculating a new target position at the control interface 174, and adjusting the position of the optics, e.g., first transmitted lens 96 and/or the prism 100. In most cases, this sequence is repeated until the minimum cross talk positions for the substrate to be inspected are found. Collecting light values allows alignment to be based directly on cross talk, rather than on secondary factors such as measuring the exact substrate thickness, etc.

After calibration, the process flow proceeds to operation 212 where inspection of the substrate begins. That is, the system begins to scan the substrate. As it scans, the objective lens movement is tracked so that the first transmitted lens can maintain a specific distance between them. In general terms, the objective position sensor triggers the first transmitted lens to move. For the most part, only the first transmitted lens moves during inspection. During or after operation 212, the process flow proceeds to operation 214 where a decision is made to re-calibrate (yes) or end the scan (no). If the decision is to re-calibrate then the process flow proceeds back to step 210. If the decision is to end scanning then the process flow proceeds to step 216, which signifies that the scan is done.

Figure 14:
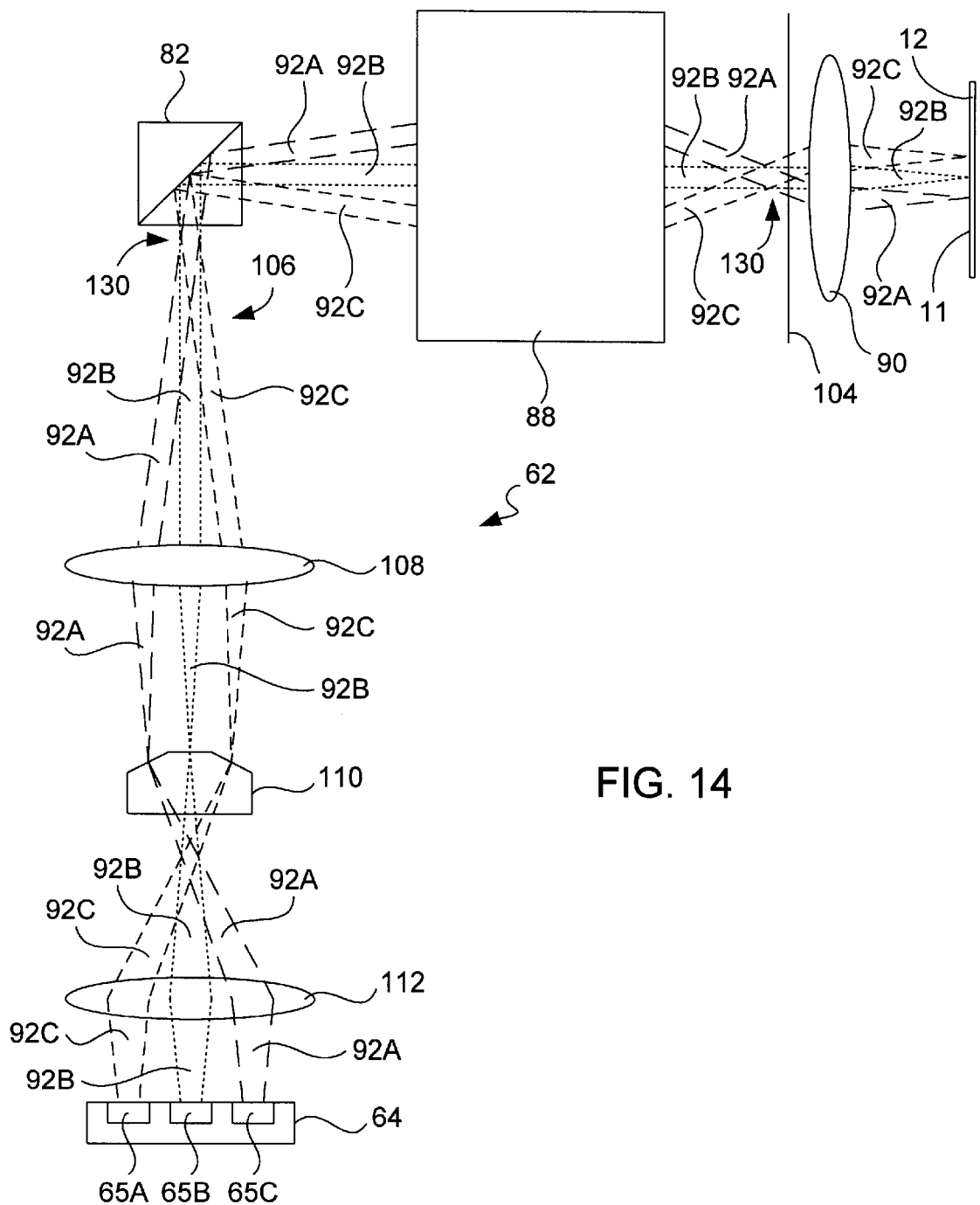
FIG. 14 is a side view diagram of the reflected light optics and reflected light detector arrangement of FIG. 3, in accordance with one embodiment of the present invention.

Referring now to FIG. 14, the reflected light optics 62 will be described in greater detail. The reflected light optics 62 are configured to receive a plurality of reflected light beams 92A–C and to direct the received beams to the reflected light detector arrangement 64. The reflected light detector arrangement 64 is configured to detect the light intensity of each of the plurality of reflected beams 92A–C. More particularly, the reflected light optics 62 are configured to perform a variety of tasks associated with the reflected beams including, but not limited to, collecting the reflected light, maintaining beam separation, and focusing the separated beams onto individual light detectors of the reflected light detector arrangement. As mentioned, prior to receiving the reflected light beams, the focused light beams produced by the inspection optics are made incident on the surface of a reflective substrate and as a result the light beams are reflected by the substrate to the reflected light optics 62. The diagram is shown in the X & Z directions such that the Y direction is coming out of (or into) the page.

Although the reflected optics are similar to the transmitted light optics, the reflected light optics are not nearly as complex. The transmitted optics 58 are a dynamic system, while the reflected optics 62 are a static system. This is generally related to the fact that the beams are reflected off the surface of the substrate, rather than being transmitted through the substrate, i.e., no plate thickness to compensate for, and that the reflected beams pass back through the objective lens, i.e., no focusing to consider because the objective is always in focus. Furthermore, only one prism is needed in the reflected optics because the reflected beams also pass back through the telescope and therefore the spot size is the same with reflected light, i.e., the magnified beam is de-magnified.

As shown in FIG. 14, the reflected light optics 62 used to receive the reflected light beams 92A–C include a portion of the inspection optics (e.g., objective lens 90, telescope 88), a quarter wave plate 104, a beam splitter cube 82, a first reflected lens 108, a second faceted prism 110, and a second reflected lens 112. The objective lens 90 is arranged to collect the diverging reflected light beams 92A–C after they reflect off the surface 11 of the substrate 12. Correspondingly, when the reflected light beams 92A–C leave the objective lens 90, they pass through the quarter wave plate 104, as they approach the telescope 88. The quarter wave plate 104 is arranged to alter the reflected light such that when the reflected light intersects the beam splitter cube 82 it is split away from the path 84. Upon leaving the quarter wave plate 104, the reflected light beams 92A–C pass through a pupil plane 130 and then the telescope 88, which reduces the size of the beams. When the beams 92A, 92B, and 92C leave the telescope 88, they are incident on the beam cube splitter 82. The beam splitter 82 is arranged to work with the quarter wave-plate 104 to direct the beams 92A, 92B, and 92C onto the path 106. As shown, the beam splitter cube 82 is positioned between the telescope 88 and the diffraction grating 76.

The beams 92A, 92B, and 92C continuing on path 106 are directed to the first reflected lens 108. As shown, the beams pass through a pupil plane 130 before reaching the first reflected lens 108. The first reflected lens 108 collects and focuses the beams, now designated 92A', 92B', and 92C' on the prism 110 (similar to the prism shown in FIGS. 10 & 11). Generally, only one lens is needed in the reflected optics, as opposed to the transmitted light optics, because the beams pass through the telescope twice (magnify/de-magnify) and therefore the spot size tends to be the same for reflected light. Similarly to the first transmitted lens 96, the first reflected lens 108 is set-up to produce well-defined spots on the prism 110. Again, the prism 110 is typically located at an image plane because that is where the beams are distinct and isolated from each other.

Furthermore, the prism 110 correspondingly bends and separates the light beams, now designated 92A"–C" such that they are separately directed towards one of the three individual detectors 65A–C. As should be appreciated, the prism 110 is used to ensure that each of the beams goes to an individual detector rather than all going to one detector. After the separated light beams 92A"–C" pass through the prism 110, they pass through the second reflected lens 112, which is arranged for focusing the separated beams onto the detectors 65A–C of the transmitted detector arrangement 64. Upon leaving the second reflected lens 112, the beams 92A"–C" are made incident on the individual detectors 64A–C. As discussed, the second reflected lens 112 focuses each of the beams 92A", 92B", 92C" on a single respective detector. For example, beam 92A" is focused onto transmission detector 65A, beam 92B" is focused onto transmission detector 65B, and beam 92C" is focused onto transmission detector 65C. As should be appreciated, each of the transmission detectors 65A, 65B, or 65C is arranged for measuring the intensity of the reflected light. Although not described in FIG. 14, it should be noted that the prism and detectors are similar to the prism and detectors described in FIGS. 9–11.

As can be seen from the foregoing, the present invention offers numerous advantages over the prior art. Different embodiments or implementations may have one or more of the following advantages. One advantage of the present invention is that faster scanning speeds can be achieved to a greater degree than possible in the prior art. By way of example, most existing inspection systems use a single beam to scan the surface of a substrate. In contrast, the present invention uses three beams to scan the surface of the substrate. The three beams produce a scanning spot distribution with about three times the scanning swath of a single beam. As such, the three beam system inspects more of the substrate per swath and is therefore about three times as fast as the single beam system. Another advantage of the present invention is that three beams are produced without the added cost of using multiple lasers, objectives, etc.

Another advantage of the present invention is that the scanning distribution provides scanning spots, which are spatially separated from one another. Spatially separating the spots ensures that the transmitted light and/or the reflected light is received at separate detectors. Another advantage of the present invention is that the system is scalable to accommodate more beams. Another advantage of the present invention is that it enables faster inspection using existing scanners and detectors, rather than using higher speed scanners and detectors that tend to have technical limitations.

Figure 15:
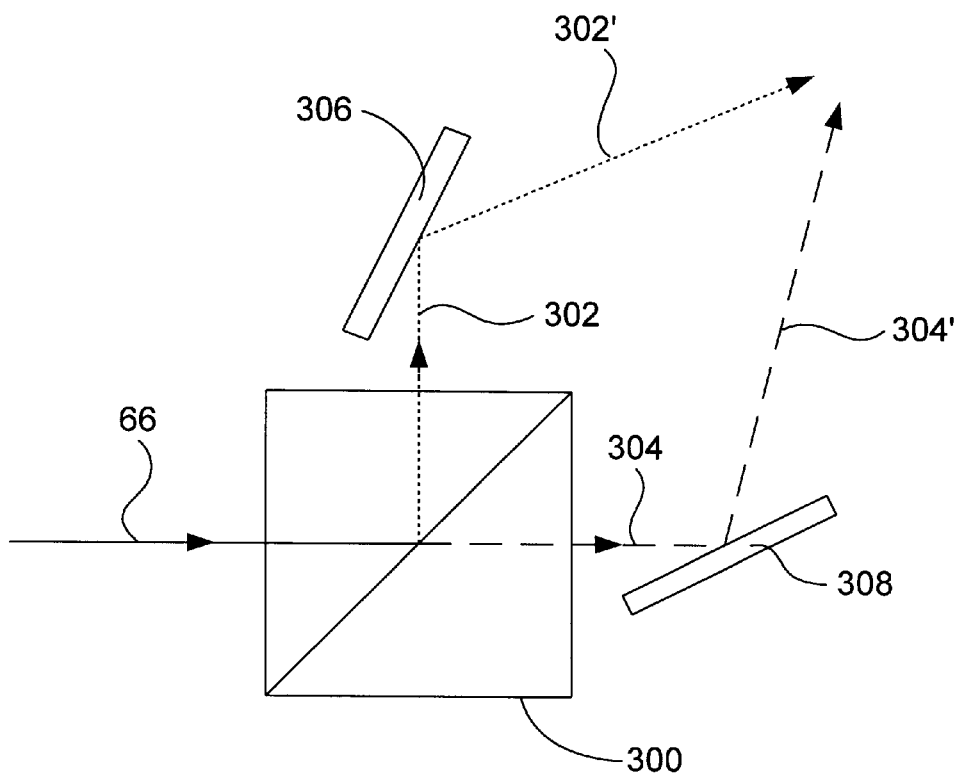
FIG. 15 is a side view diagram of a beam separator utilizing a beam splitter cube, in accordance to an alternate embodiment of the present invention.
Figure 16:
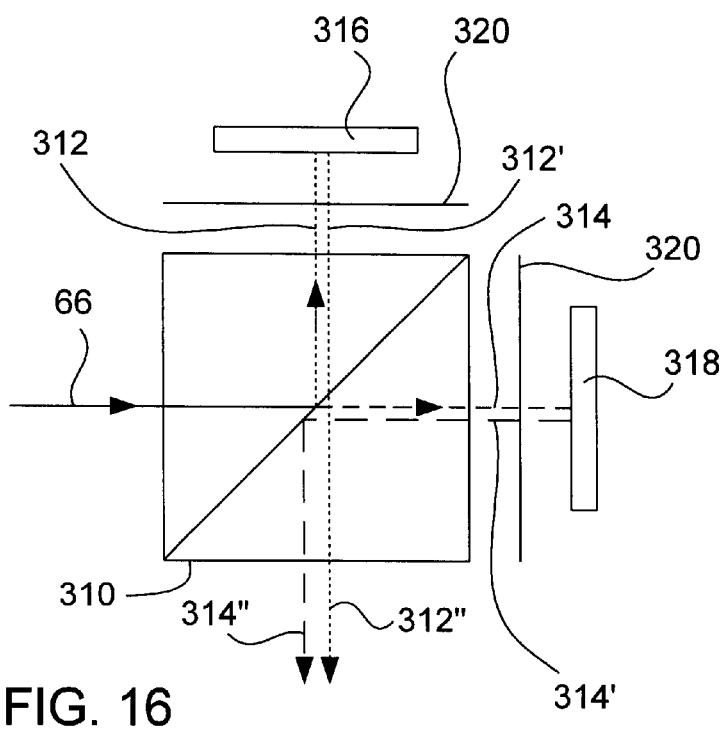
FIG. 16 is a side view diagram of a beam separator utilizing a beam splitter cube, in accordance to an alternate embodiment of the present invention.

While this invention has been described in terms of several preferred embodiments, there are alterations, permutations, and equivalents, which fall within the scope of this invention. For example, in an alternate embodiment, a beam splitter cube may be used to separate the single light beam into a plurality of light beams, and a mirror system may be used to direct the separated beams onto an optical path for scanning the surface of a substrate. FIG. 15 shows one implementation of this embodiment. In FIG. 15, the single beam 66 is made incident on a beam splitter cube 300, which divides the single beam 66 into beams 302 and 304. The beams 302 and 304 are then made incident on mirrors 306 and 308, respectively, which redirect each of the beams, now designated 302' and 304', to a new optical path. Although only two beams are shown, additional beam splitter cubes could be used to produce more beams. FIG. 16 shows another implementation of the aforementioned embodiment. In FIG. 16, the single beam 66 is made incident on a beam splitter cube 310, which divides the single beam into beams 312 and 314. The beams 312 and 314 are then made incident on mirrors 316 and 318, respectively, which redirect each of the beams, now designated 312' and 314', back towards the beam splitter cube 310. Before the redirected beams 316' and 318' reach the beam splitter cube 310, however, they each pass through a quarter wave plate 320 that works with the beam splitter cube 310 to redirect each of the beams, now designated 312" and 314", onto a new optical path.

Furthermore, it should also be noted that there are many alternative ways of implementing the methods and apparatuses of the present invention. By way of example, the techniques described could also be used in systems that inspect optical disks, magnetic disks and optical substrates. It is therefore intended that the following appended claims be interpreted as including all such alterations, permutations, and equivalents as fall within the true spirit and scope of the present invention.

What is claimed is:

1. An optical inspection system for inspecting the surface of a substrate, comprising:
   a light source for emitting a light beam along an optical axis;
   a first set of optical elements arranged for separating the light beam into a plurality of light beams, directing the plurality of light beams to intersection with the surface of the substrate, and focusing the plurality of light beams to a plurality of scanning spots on the surface of the substrate;
   a second set of optical elements adapted for collecting a plurality of transmitted light beams caused by the intersection of the plurality of light beams with the surface of the substrate and by passing the plurality of light beams through the substrate, the second set of optical elements including at least a lens arrangement and a prism;
   a light detector arrangement including individual light detectors that each receive individual ones of the plurality of transmitted light beams, the light detectors being arranged for sensing the light intensity of the transmitted light beams, wherein the lens arrangement focuses the plurality of transmitted light beams onto the prism, and the prism directs the individual ones of the plurality of transmitted light beams towards the individual light detectors of the light detector arrangement; and
   a control system for controlling the optical components of the first and second optical elements, and for receiving scan signals from each of the light detectors of the light detector arrangement.

2. The optical inspection system as recited in claim 1 wherein the lens arrangement includes a first transmitted lens and a spherical aberration correction lens, the first transmitted lens being arranged for collecting and focusing the plurality of transmitted light beams, the spherical aberration correction lens being arranged for maintaining image quality of the plurality of transmitted light beams.

3. The optical inspection system as recited in claim 2 wherein the first transmitted lens and the spherical aberration correction lens are moved along the optical axis to compensate for a varying range of substrate thickness.

4. The optical inspection system as recited in claim 1 wherein the prism includes a plurality of facets that correspond to each of the plurality of transmitted light beams, each facet being arranged for directing an individual one of the plurality of light beams towards a corresponding individual light detector of the light detector arrangement.

5. The optical inspection system as recited in claim 4 wherein the transmitted light optics include an second transmitted lens for focusing the individual ones of the plurality of transmitted light beams onto the corresponding individual light detector of the light detector arrangement.

6. The optical inspection system as recited in claim 1 wherein the second set of optical elements comprises reflected light optics for collecting light that is reflected off the surface of the substrate under inspection.

7. The optical inspection system as recited in claim 6 wherein the reflected light optics include at least a first reflected lens and a prism, wherein the first reflected lens is arranged for focusing the plurality of transmitted light beams onto the prism, and wherein the prism is arranged for directing individual ones of the transmitted light beams towards individual detectors of the light detector arrangement.

8. The optical inspection system as recited in claim 7, wherein the prism includes a plurality of facets that correspond to each of the plurality of reflected light beams, each facet being arranged for directing an individual one of the plurality of light beams towards a corresponding individual light detector of the light detector arrangement.

9. The optical inspection system as recited in claim 8 wherein the reflected light optics further include a second transmitted lens for focusing the individual ones of the plurality of transmitted light beams onto the corresponding individual light detector of the light detector arrangement.

10. The optical inspection system as recited in claim 6 wherein a portion of the first optical elements are included in the reflected light optics.

11. The optical inspection system as recited in claim 6 wherein the optical inspection system is configured to perform reflected light inspection where the amount of light reflected from the substrate is measured via the light detector arrangement.

12. The optical inspection system as recited in claim 6 wherein the optical inspection system is configured to perform simultaneous transmitted and reflected light inspection where the amount of light transmitted through the substrate and the amount of light reflected from the substrate is measured via the light detector arrangement.

13. The system as recited in claim 1 wherein the substrate is a mask, reticle or semiconductor wafer.

14. The system as recited in claim 1 wherein the system is capable of inspecting for defects on the surface of the substrate.

15. The system as recited in claim 1 wherein the first set of optical elements includes a diffraction grating or beam splitter cube.

16. The system as recited in claim 1 wherein the first set of optical elements includes a variable magnification subsystem disposed along the optical axis, the variable magnification subsystem being arranged for controlling the scanning spot size.

17. The optical inspection system as recited in claim 1 wherein the optical inspection system is configured to perform transmitted light inspection where the amount of light transmitted through the substrate is measured via the light detector arrangement.

18. The optical inspection system as recited in claim 1 wherein the first set of optical elements includes a mechanism for sweeping the plurality of light beams so as to move the plurality of scanning spots along the surface of the substrate, the plurality of light beams working together to increase the speed of inspection.

19. An optical inspection system for inspecting a surface of a substrate, comprising:
   a transmitted light optical arrangement disposed along an optical axis and including at least a first lens and second lens, both of which are arranged to move along the optical axis, and a prism, which is arranged to move orthogonal to the optical axis, the transmitted light optical arrangement being arranged for directing a plurality of transmitted light beams, which are formed by scanning the substrate with a plurality of light beams, onto a plurality of light detectors; and
   a control system for controlling the transmitted light optical arrangement so as to maintain separation of the plurality of beams on the light detectors, the control system including at least a first lens drive, a second lens drive and a prism drive, all of which are coupled to a control interface, which is arranged to control the drives, the first lens drive is arranged to actuate the movement of the first lens, the second lens drive is arranged to actuate the movement of the second lens, and the prism drive is arranged to actuate the movement of the prism.

20. The optical inspection system as recited in claim 19 wherein the first lens, the second lens and the prism each have nominal positions, which are based at least in part on the magnification level of the plurality of beams.

21. The optical inspection system as recited in claim 19 wherein the first lens, the second lens and the prism each have nominal positions, which are based at least in part on the thickness of the substrate.

22. The optical inspection system as recited in claim 21 wherein the nominal positions of the first lens and the prism are calibrated for each substrate to be inspected, and wherein the calibrated positions are based at least in part on measured cross talk values.

23. The optical inspection system as recited in claim 22 wherein the calibration is performed automatically, without information or assistance from an operator.

24. The optical inspection system as recited in claim 19 wherein the first lens is arranged to track the surface of the substrate during inspection.

25. The optical inspection system as recited in claim 24 wherein the tracking is calibrated and performed automatically, without information or assistance from an operator.

26. The system as recited in claim 19 wherein the substrate is a mask, reticle or semiconductor wafer.

* * * * *